(12) United States Patent
Wang et al.

(10) Patent No.: US 8,486,981 B2
(45) Date of Patent: Jul. 16, 2013

(54) SELECTIVE LIGANDS FOR THE DOPAMINE 3 ($D_3$) RECEPTOR AND METHODS OF USING THE SAME

(75) Inventors: Shaomeng Wang, Saline, MI (US);
Jianyong Chen, Ann Arbor, MI (US);
Gregory Collins, Medford, MA (US);
Beth Levant, Kansas City, MO (US);
James H. Woods, Ann Arbor, MI (US)

(73) Assignees: The Regents of the University of Michigan, Ann Arbor, MI (US);
University of Kansas, Lawrence, KS (US)

( * ) Notice: Subject to any disclaimer, the term of this patent is extended or adjusted under 35 U.S.C. 154(b) by 0 days.

(21) Appl. No.: 13/406,803

(22) Filed: Feb. 28, 2012

(65) Prior Publication Data

US 2012/0232118 A1    Sep. 13, 2012

Related U.S. Application Data

(60) Provisional application No. 61/450,885, filed on Mar. 9, 2011.

(51) Int. Cl.
| | |
|---|---|
| *A61K 31/4245* | (2006.01) |
| *A61K 31/428* | (2006.01) |
| *C07D 271/06* | (2006.01) |
| *C07D 277/82* | (2006.01) |

(52) U.S. Cl.
USPC ............ 514/364; 514/367; 548/131; 548/178

(58) Field of Classification Search
None
See application file for complete search history.

(56) References Cited

U.S. PATENT DOCUMENTS

2011/0184033 A1 * 7/2011 Wang et al. .................. 514/367

OTHER PUBLICATIONS

Chen, J.; Collins, G. T.; Zhang, J.;Yang, C-.Y.; Levant, B.; Woods, J.; Wang, S. Design, Synthesis, and Evaluation of Potent and Selective Ligands for the Dopamine 3 (D3) receptor with a Novel in Vivo Behavioral Profile. Journal of Medicinal Chemistry, 2008, 51, 5905-5908.*

Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*

* cited by examiner

*Primary Examiner* — Michael Barker
*Assistant Examiner* — Po-Chih Chen
(74) *Attorney, Agent, or Firm* — Marshall, Gerstein & Borun LLP

(57) ABSTRACT

Potent and selective ligands for the dopamine 3 ($D_3$) receptor are disclosed. The $D_3$ receptor ligands have a structural formula:

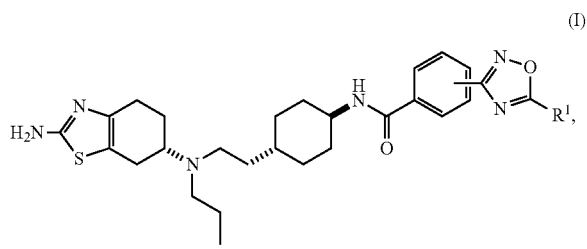

wherein $R^1$ is $C_{1-6}$ alkyl or $C_{3-6}$ cycloalkyl; or

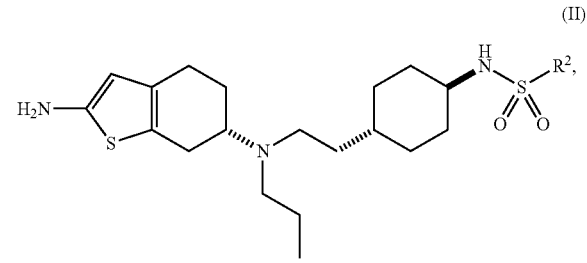

wherein $R^2$ is

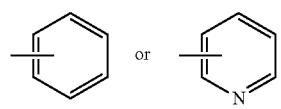

substituted with one or two halogen(s) or $OC_{1-3}$alkyl.

15 Claims, 2 Drawing Sheets

SELECTIVE LIGANDS FOR THE DOPAMINE 3 ($D_3$) RECEPTOR AND METHODS OF USING THE SAME

CROSS REFERENCE TO RELATED APPLICATION

This application claims the benefit of U.S. Provisional Patent Application No. 61/450,885, filed Mar. 9, 2011, incorporated herein in its entirety.

STATEMENT OF GOVERNMENTAL INTEREST

This invention was made with government support under Grant No. R01DA020669, awarded by the National Institute of Drug Abuse, National Institutes of Health. The government has certain rights in the invention.

FIELD OF THE INVENTION

The present invention relates to ligands for the dopamine 3 ($D_3$) receptor and to therapeutic methods of treating conditions and diseases wherein modulation of the $D_3$ receptor provides a benefit.

BACKGROUND OF THE INVENTION

Dopamine (DA) is a neurotransmitter that plays an essential role in normal brain functions. As a chemical messenger, dopamine is similar to adrenaline. In the brain, dopamine is synthesized in the pre-synaptic neurons and released into the space between the pre-synaptic and post-synaptic neurons.

Dopamine affects brain processes that control movement, emotional response, and ability to experience pleasure and pain. Therefore, the regulation of dopamine plays an important role in mental and physical health. Neurons containing dopamine are clustered in the midbrain area called the substantia nigra. Abnormal dopamine signaling in the brain has been implicated in a substantial number of pathological conditions, including drug (e.g., cocaine) abuse, depression, anxiety, schizophrenia, Tourette's syndrome, eating disorders, alcoholism, chronic pain, obsessive compulsive disorders, restless leg syndrome, Parkinson's Disease, and the like.

Dopamine molecules bind to and activate dopamine receptors on the post-synaptic neurons. Dopamine molecules then are transported through the dopamine transporter protein (DAT) back into the pre-synaptic neurons, where they are metabolized by monoamine oxidase (MAO). In conditions such as cocaine abuse, cocaine binds to the dopamine transporter and blocks the normal flow of dopamine molecules. Excess concentrations of dopamine cause over-activation of dopamine receptors. In other conditions, such as Parkinson's Disease, lack of sufficient dopamine receptors in the brain causes insufficient activation of dopamine receptors.

Dopaminergic neurotransmission is mediated by five dopamine receptors ($D_1$-$D_5$), which can be grouped into the $D_1$-like ($D_1$ and $D_5$) and $D_2$-like ($D_2$, $D_3$, and $D_4$) receptor subtypes. The dopamine 3 ($D_3$) subtype receptor has been implicated as an important target for agents currently used clinically for the treatment of schizophrenia, Parkinson's disease, depression, and other neurological diseases.[1]-[4] Studies have also provided strong evidence that potent and selective $D_3$ ligands may have a therapeutic potential as pharmacotherapies for the treatment of drug abuse.[5]-[8] Therefore, considerable effort has been devoted to the discovery and development of potent and selective $D_3$ ligands.[7]-[33]

A number of representative potent and selective $D_3$ ligands (antagonists, partial agonists and full agonists) are shown in FIG. 1. These $D_3$ ligands bind to the $D_3$ receptor with a very high affinity ($K_i$ values of ≦1.0 nM) and display a selectivity of 100-500 times over the $D_2$ receptor and greater than 1,000 over the $D_1$-like receptors when evaluated in in vitro binding assays either using cloned human dopamine receptors or rat brain.[7],[8]

SB-277011A (1) is a potent and selective $D_3$ antagonist[9] and has been used extensively in animals to investigate the role of the $D_3$ receptor in drug abuse.[8] One disadvantage of SB-277011A is that relatively high doses are needed to produce an in vivo effect, suggesting a moderate central nervous system (CNS) penetration. SB-414796 (2) is a potent and selective $D_3$ antagonist and has an excellent bioavailability in the rat and a good CNS penetration.[16] However, compound 2 did not advance into clinical development because of its inhibition of p450 and its potential cardiotoxicity due to a strong binding to hERG potassium channel.[8],[32] Very recently, compound 3 was designed as a highly potent and selective $D_3$ antagonist.[32] Compound 3 has an excellent oral bioavailability and good CNS penetration. Importantly, compound 3 only shows weak inhibition on all the P450 isoforms and a large selectivity window with respect to their affinity at the hERG channel, overcoming the major issues associated with compound 2. BP 897 (4) initially was described as a potent $D_3$ partial agonist with a modest selectivity of less than 100-times over $D_2$,[6] but subsequent studies have shown that compound 4 may behave as an $D_3$ antagonist.[34],[35] NGB 2904 (5) is a potent and selective $D_3$ antagonist[10] and has been extensively used in vivo evaluations, despite its poor aqueous solubility.[8] In order to improve $D_3$ selectivity and water solubility, a large number of new analogues have been designed and synthesized, including compounds 6,[18], 7[30] and 8[30]. Compound 8 is a potent $D_3$ antagonist and displays a selectivity of greater than 400-fold over $D_2$ in in vitro binding assays.[30] Compound 8 has a much improved solubility compared to compound 5.[30]

One challenge in the design and development of $D_3$ ligands has been a lack of the correlation between the intrinsic in vitro activity and in vivo activity for many reported $D_3$ ligands. This was due in part to a lack of well validated in vivo functional assays for the $D_3$ and $D_2$ receptors. To this end, yawning and hypothermia functional assays for the $D_3$ and $D_2$ receptors in the rat have been validated.[36],[37] Data clearly show that while $D_3$ agonist activity induces yawning in the rat, $D_2$ agonist activity inhibits yawning induced by the $D_3$ agonist activity.[36],[37] Furthermore, while $D_2$ agonist activity decreases the body core temperature in the rat, $D_3$ agonist activity has no effect on the body core temperature.[36],[37]

A number of known $D_3$ ligands were evaluated in the yawning and hypothermia assays. It was found that many of the potent and selective $D_3$ ligands based upon in vitro data, such as compounds 1, 4, 5 and 9, have a narrow range of selectivity in vivo at the $D_3$ receptor over the $D_2$ receptor, typically less than 10-fold.[36],[37] This narrow range of in vivo selectivity for the $D_3$ receptor over the $D_2$ receptor makes the interpretation of in vivo behavioral data for many known $D_3$ ligands complicated and highlights the need for highly potent $D_3$ ligands with a large in vivo selectivity for $D_3$ over $D_2$.

Many reported potent and selective $D_3$ ligands based upon their in vitro data have very poor aqueous solubility, which contributes to their low in vivo activity and selectivity.[7],[8] To address the solubility issue, a series of new compounds based upon the core structure of pramipexole (compound 9), a highly potent $D_3$ full agonist with excellent aqueous solubility but a modest selectivity for the $D_3$ receptor over the $D_2$ receptor, were designed and synthesized.[25] Another consideration for using pramipexole as the basic core structure is that pramipexole is an FDA approved drug for the treatment of Parkinson's disease and restless leg syndrome, and has an excellent safety and pharmacological properties in the human.

Accordingly, a need still exists in the art for potent and selective $D_3$ ligands having physical and pharmacological properties that permit use of the ligands in therapeutic applications. The present invention provides ligands designed not only to selectively bind to the $D_3$ receptor subtype in in vitro binding assays, but also modulate (e.g., agonism and/or antagonism) the $D_3$ receptor with high selectivity in vivo functional assays in the rat.

SUMMARY OF THE INVENTION

The present invention is directed to potent and selective ligands for $D_3$ receptors and to methods of using the ligands in a therapeutic treatment of conditions and diseases wherein modulation of the $D_3$ receptors provides a benefit. More particularly, the present invention is directed to compounds having a structural formula (I) and (II):

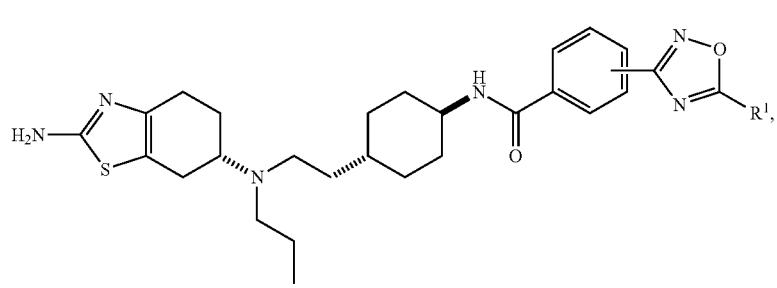

wherein $R^1$ is $C_{1-6}$ alkyl or $C_{3-6}$ cycloalkyl;

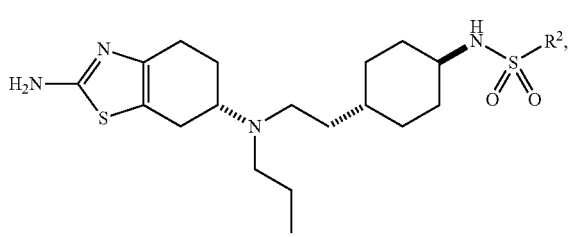

wherein $R^2$ is

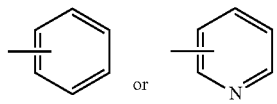

substituted with one or two halogen(s) or $OC_{1-3}$alkyl.

In one embodiment, the present invention provides a method of treating a condition or disease by administering a therapeutically effective amount of a compound of structural formula (I) or (II) to an individual in need thereof. The disease or condition of interest is treatable by modulation of $D_3$ receptors, such as, for example, drug abuse, Parkinson's disease, restless leg syndrome, schizophrenia, and depression.

Another embodiment of the present invention is to provide a composition comprising a $D_3$ receptor ligand of structural formula (I) or (II) and an excipient and/or pharmaceutically acceptable carrier useful in treating diseases or conditions wherein modulation of $D_3$ receptors provides a benefit, i.e., a disease or condition of interest.

Another embodiment of the present invention is to utilize a composition comprising a compound of structural formula (I) or (II) and a second therapeutically active agent in a method of treating an individual for a disease or condition wherein modulation of $D_3$ receptors provides a benefit.

In a further embodiment, the invention provides for use of a composition comprising a $D_3$ ligand of structural formula (I) or (II) and an optional second therapeutic agent for the manufacture of a medicament for treating a disease or condition of interest, e.g., drug abuse, Parkinson's disease, restless leg syndrome, schizophrenia, and depression.

Still another embodiment of the present invention is to provide a kit for human pharmaceutical use, comprising (a) a container, (b1) a packaged composition comprising a $D_3$ ligand of structural formula (I) or (II) and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

The $D_3$ ligand of structural formula (I) or (II) and the second therapeutic agent can be administered together as a single-unit dose or separately as multi-unit doses, wherein the $D_3$ ligand of structural formula (I) or (II) is administered before the second therapeutic agent or vice versa. It is envisioned that one or more dose of the $D_3$ ligand of structural formula (I) or (II) or one and/or more dose of the second therapeutic agent can be administered.

In one embodiment, the $D_3$ ligand of structural formula (I) or (II) and second therapeutic agent are administered simultaneously. In related embodiments, the $D_3$ ligand of structural formula (I) or (II) and second therapeutic agent are administered from a single composition or from separate compositions. In a further embodiment, the $D_3$ ligand of structural formula (I) or (II) and second therapeutic agent are administered sequentially. The $D_3$ ligand of structural formula (I) or (II), as used in the present invention, can be administered in an amount of about 0.005 to about 500 milligrams per dose, about 0.05 to about 250 milligrams per dose, or about 0.5 to about 100 milligrams per dose.

In one preferred embodiment, the present invention provides a method of treating a subject having a disease, addiction, or other pathological condition (e.g., cocaine abuse, depression, anxiety, an eating disorder, alcoholism, chronic pain, obsessive compulsive disorder, schizophrenia, restless leg syndrome (RLS), Parkinson's disease, and the like) comprising administering to the subject a therapeutic dose of a compound of structural formula (I) or (II) or a composition containing the compound.

These and other aspects and features of the present invention will become apparent from the following drawings and detailed description of the preferred embodiments.

DETAILED DESCRIPTION OF THE PREFERRED EMBODIMENTS

Figure 1:
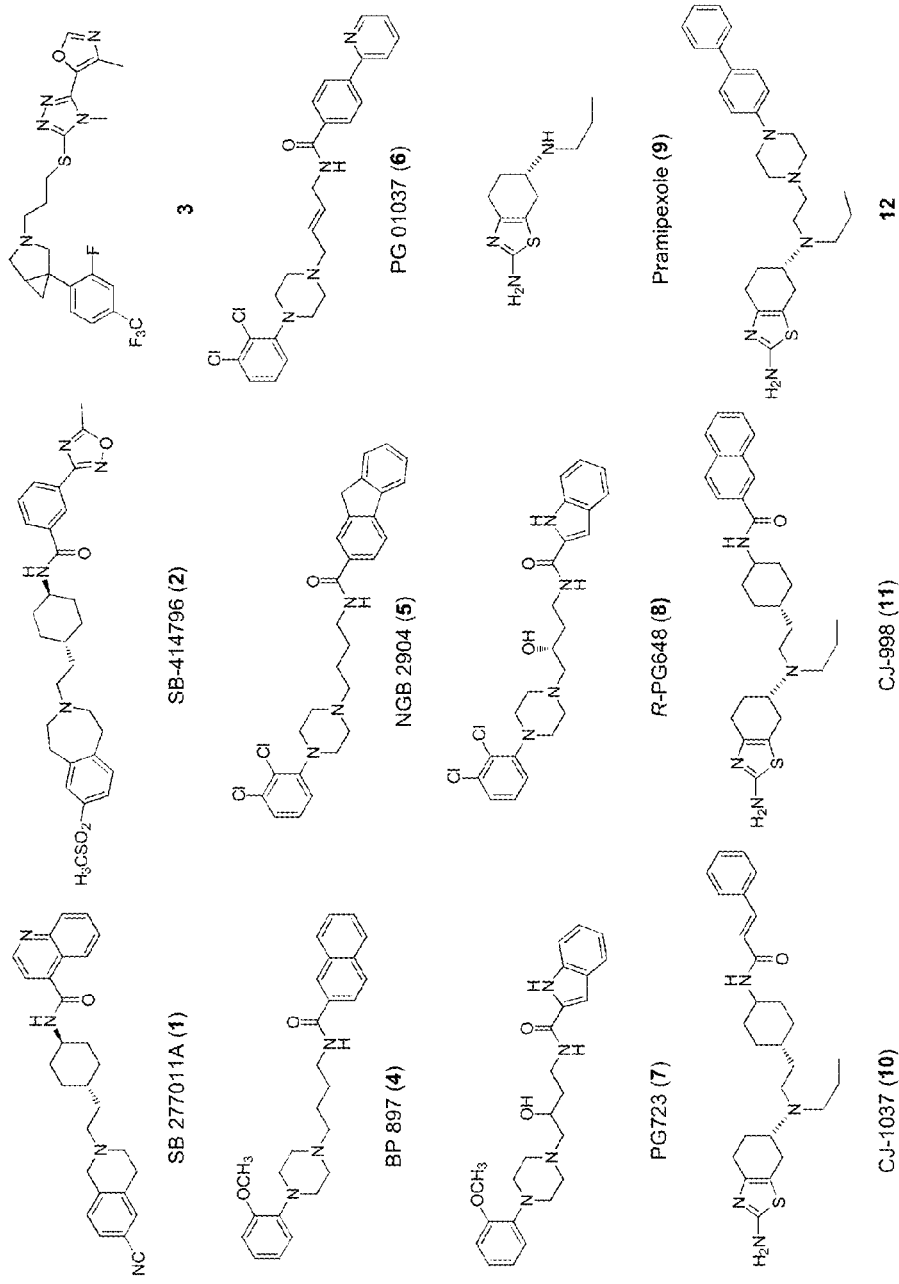
FIG. 1 contains the chemical structures of known $D_3$ ligands.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

As used herein, the terms "$D_3$ ligand" or "$D_3$ receptor ligand" are used interchangeably.

As used herein, the terms "treat," "treating," "treatment," and the like refer to eliminating, reducing, or ameliorating a disease or condition and/or symptoms associated therewith. Although not precluded, treating a disease or condition does not require that the disease, condition or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the invention, to efficaciously deliver the agents for the treatment of condition or disease of interest to an individual in need thereof.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration" and similar phrases mean that a composition comprising two or more agents are administered concurrently to the subject being treated. By "concurrently," it is meant that each agent is administered simultaneously or sequentially in any order at different points in time. However, if not administered simultaneously, they are, in one aspect, administered sufficiently closely in time so as to provide the desired treatment effect of the combination of agents. Suitable dosing intervals and dosing order of the agents will be readily apparent to those skilled in the art. It also is contemplated that two or more agents are administered from separate compositions, and in one aspect, one composition is administered prior to administration of the other composition. Prior administration refers to administration of the agents within one day (24 hours). It is further contemplated that one agent is administered subsequent to administration of the other agent. Subsequent administration is meant to describe administration from 30 minutes of the second agent up to one day (24 hours) after administration of the first agent. Within 24 hours may include administration after 30 minutes, 1, 2, 3, 4, 5, 6, 7, 8, 9, 10, 11, 12, 16, 20, or 24 hours.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illustrate the invention and is not a limitation on the scope of the invention unless otherwise claimed. No language in the specification should be construed as indicating any non-claimed element as essential to the practice of the invention.

The present invention is directed to potent and selective ligands for the $D_3$ receptor ligand having a structural formula (I) or (II):

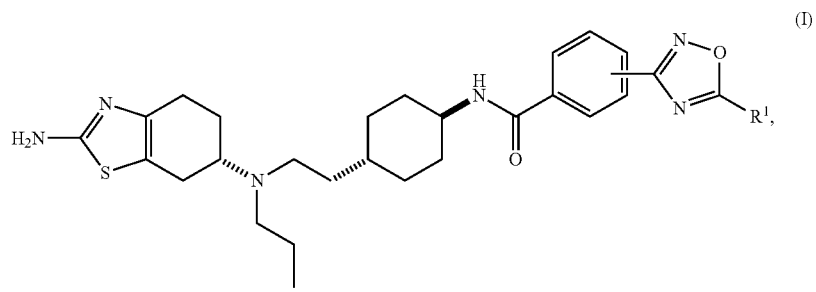

wherein R¹ is $C_{1-6}$ alkyl or $C_{3-6}$cycloalkyl;

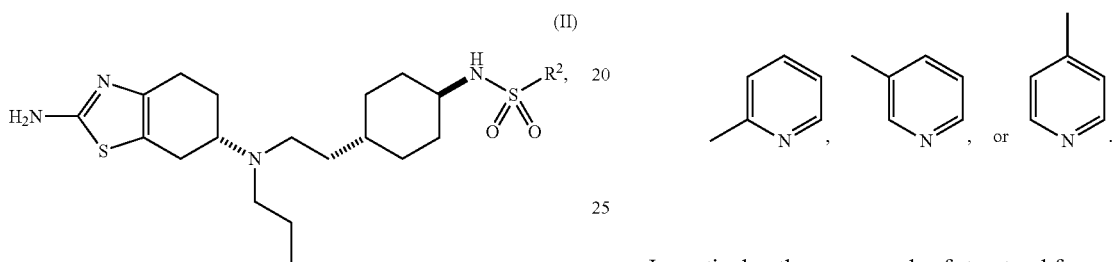

wherein R² is

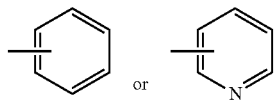

substituted with one or two halogen(s) or $OC_{1-3}$alkyl.

In two embodiments, the compounds of structural formula (I) have the following structure:

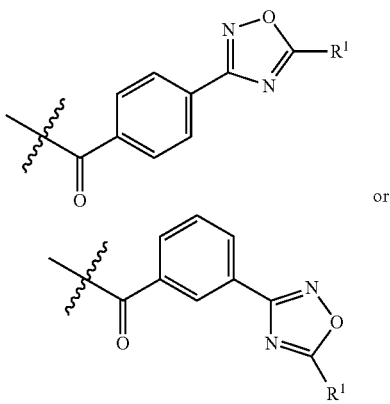

A compound of structural formula (II) can contain one or two halogen, one or two $OC_{1-3}$alkyl, or one halogen and one $OC_{1-3}$alkyl.

The R² of structural formula (II) can be

In particular, the compounds of structural formula (I) and (II) are used in methods of treating a disease or condition wherein modulation of the $D_3$ receptor provides a benefit, for example drug (e.g., cocaine) abuse, depression, anxiety, schizophrenia, Tourette's syndrome, eating disorders, alcoholism, restless leg syndrome, Parkinson's disease, obsessive compulsive disorder, and chronic pain. The method comprises administering a therapeutically effective amount of a compound of structural formula (I) or (II) to an individual in need thereof. The present methods also encompass administering a second therapeutic agent to the individual in addition to the compound of structural formula (I) or (II). The second therapeutic agent is selected from drugs known as useful in treating the disease or condition afflicting the individual in need thereof.

As used herein, the term "alkyl" refers to straight chained and branched saturated hydrocarbon groups, nonlimiting examples of which include methyl, ethyl, and straight chain and branched propyl, butyl, pentyl, and hexyl groups.

As used herein, the term "halo" means fluoro, chloro, bromo, and iodo.

As used herein, the term "$C_{3-6}$cycloalkyl" means a monocyclic aliphatic ring containing three to six carbon atoms.

Additionally, salts, hydrates, and solvates of the compounds disclosed herein also are included in the present disclosure and can be used in the methods disclosed herein. For example, an acid salt of a compound of structural formula (I) or (II) can be obtained, by reacting the compound with a suitable organic or inorganic acid, such as hydrogen chloride, hydrogen bromide, acetic acid, perchloric acid, and the like. Examples of such salts include, but are not limited to, hydrochlorides, hydrobromides, sulfates, methanesulfonates, nitrates, maleates, acetates, citrates, fumarates, tartrates, bisulfates, phosphates, besylates, malates, gluconates, saccharates, pamoates, succinates, benzoates and salts of amino acids, such as glutamic acid.

Specific compounds of the present invention include, but are not limited to, the following:

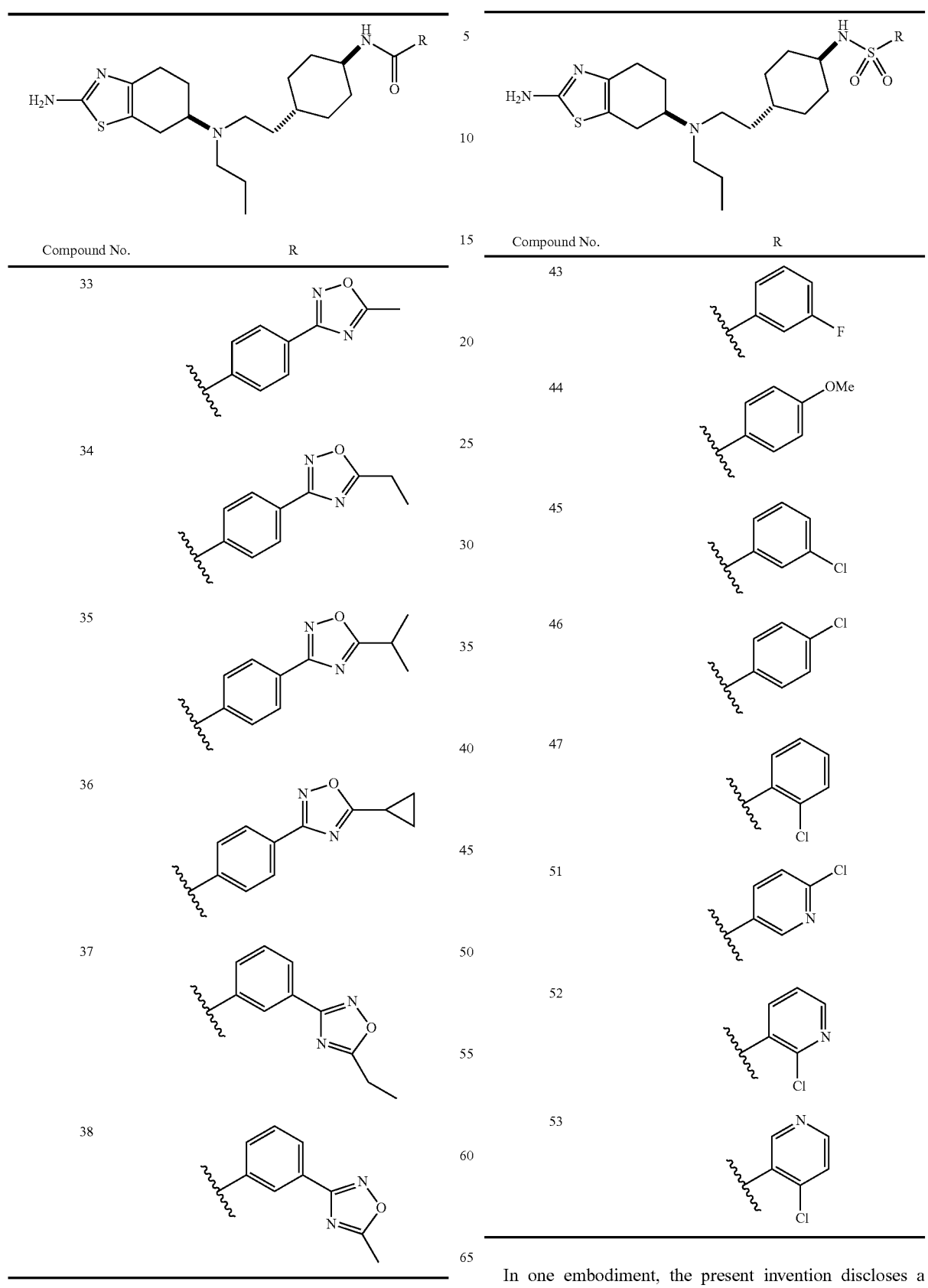

condition wherein modulation of the $D_3$ receptor provides a benefit comprising administering a therapeutically effective amount of a compound of structural formula (I) or (II) to an individual in need thereof.

The methods described herein relate to the use of a compound of structural formula (I) or (II) and an optional second therapeutic agent useful in the treatment of diseases and conditions wherein modulation of the $D_3$ receptor provides a benefit. The method of the present invention can be accomplished by administering a compound of structural formula (I) or (II) as the neat compound or as a pharmaceutical composition. Administration of the pharmaceutical composition, or neat compound of structural formula (I) or (II), can be performed during or after the onset of the disease or condition of interest. Typically, the pharmaceutical compositions are sterile, and contain no toxic, carcinogenic, or mutagenic compounds that would cause an adverse reaction when administered.

A compound of structural formula (I) or (II) also can be administered in conjunction with a second therapeutic agent useful in the treatment of a disease or condition wherein modulation of the $D_3$ receptor provides a benefit. The second therapeutic agent is different from the compound of structural formula (I) and (II). A compound of structural formula (I) or (II) and the second therapeutic agent can be administered simultaneously or sequentially. In addition, the compound of structural formula (I) or (II) and second therapeutic agent can be administered from a single composition or two separate compositions. A compound of structural formula (I) or (II) and the optional second therapeutic agent can be administered simultaneously or sequentially to achieve the desired effect.

The second therapeutic agent is administered in an amount to provide its desired therapeutic effect. The effective dosage range for each second therapeutic agent is known in the art, and the second therapeutic agent is administered to an individual in need thereof within such established ranges.

The present invention therefore is directed to compositions and methods of treating diseases or conditions wherein modulation of the $D_3$ receptor provides a benefit. The present invention also is directed to pharmaceutical compositions comprising a compound of structural formula (I) and/or (II) and a second therapeutic agent useful in the treatment of diseases and conditions wherein modulation of the $D_3$ receptor provides a benefit. Further provided are kits comprising a compound of structural formula (I) or (II) and, optionally, a second therapeutic agent useful in the treatment of diseases and conditions wherein modulation of the $D_3$ receptor provides a benefit, packaged separately or together, and an insert having instructions for using these active agents.

As demonstrated below, compounds of structural formula (I) and (II) are a potent and selective ligands for the $D_3$ receptor and can be used in treating diseases and conditions, like drug abuse and restless leg syndrome, where modulation of the $D_3$ receptor provides a benefit.

A compound of structural formula (I) or (II) used in a method of the present invention can be administered in an amount of about 0.005 to about 500 milligrams per dose, about 0.05 to about 250 milligrams per dose, or about 0.5 to about 100 milligrams per dose. For example, a compound of structural formula (I) or (II) can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

A compound of structural formula (I) or (II) can be formulated in suitable excipients for oral administration or for parenteral administration. Such excipients are well known in the art. A compound of structural formula (I) or (II) typically is present in such a composition in an amount of about 0.1% to about 75% by weight of the composition.

A compound of structural formula (I) or (II) and the second therapeutic agent can be administered together as a single-unit dose or separately as multi-unit doses, wherein the compound of structural formula (I) or (II) is administered before the second therapeutic agent or vice versa. One or more dose of the compound of structural formula (I) or (II) and/or one or more dose of the second therapeutic agent can be administered.

The compounds of structural formula (I) or (II) therefore can be used in conjunction with one or more second therapeutic agents, for example, but not limited to, antipsychotic agents (e.g., clozapine, olanzapine, quetiapine, risperidone, ziprasidone, haloperidol, and aripiprazole), antidepressant agents, such as tricyclic antidepressants (e.g., amitriptyline, dothiepin, doxepin, trimipramine, butriptyline, clomipramine, desipramine, imipramine, iprindole, lofepramine, nortriptyline, and protriptyline), monoamine oxidase inhibitors (e.g., isocarboxazid, phenelzine, and tranylcyclopramine), 5-HT reuptake inhibitors (e.g., fluvoxamine, sertraline, fluoxetine, and paroxetine), serotonin-1 B antagonists (e.g., elzasonan), serotonin-2A antagonists (e.g., eplivanserin and MDL-100907), histamine-3 antagonists or agonists (e.g., cipralisant, ABT239, TISQ, and GSK-189254A) and/or with antiparkinsonian agents such as dopaminergic antiparkinsonian agents (e.g., levodopa, preferably in combination with a peripheral decarboxylase inhibitor e.g., benserazide or carbidopa, or with a dopamine agonist, e.g., bromocriptine, lysuride, and pergolide).

The compounds of structural formula (I) and (II) are highly selective dopamine $D_3$ receptor ligands which, because of their low affinity for other receptors such as dopamine $D_1$ and $D_2$, give rise to fewer side effects than compounds that are non-selective $D_2/D_3$ ligands (agonists, partial agonists, antagonists, or inverse agonists). Compounds of the present invention can be selective agonists, partial agonists, antagonists or inverse agonists for the $D_3$ receptor over other dopamine receptors.

The present invention provides a selective $D_3$ ligand, as exemplified by compounds of structural formula (I) and (II), for the treatment of a variety of diseases and conditions, in which selective modulation of the $D_3$ receptor has a beneficial effect. Preferably, a compound of structural formula (I) or (II) is selective for the $D_3$ receptor over the $D_2$ receptor by a factor of at least 250, and over the $D_1$ receptor by a factor of at least 10,000.

Conditions and diseases of the central nervous system (CNS) are understood as meaning disorders which affect the spinal cord and, in particular, the brain. Within the meaning of the present invention, the term "disease" or "condition" denote disturbances and/or anomalies that as a rule are regarded as being pathological conditions or functions, and that can manifest themselves in the form of particular signs, symptoms, and/or malfunctions. The treatment methods according to the invention can be directed toward individual disorders, i.e. anomalies or pathological conditions, but it also is possible to treat several anomalies that may be causatively linked to each other to be combined into patterns, i.e., syndromes.

The diseases and conditions that can be treated in accordance to the invention include, for example, psychiatric and neurological disturbances. These diseases and conditions include, for example, organic disturbances, including symptomatic disturbances, such as psychoses of the acute exogenous reaction type or attendant psychoses or organic or exogenous cause, e.g., in association with metabolic disturbances, infections, and endocrinopathologies; endogenous psychoses, such as schizophrenia and schizotype and delusional disturbances; affective disturbances, such as depressions, mania, and/or manic-depressive conditions; and also mixed forms of the above described diseases and conditions; neurotic and somatoform disturbances and disturbances in association with stress; dissociative disturbances, e.g., loss of consciousness, clouding of consciousness, double consciousness, and personality disturbances; disturbances in attention and waking and/or sleeping behavior, such as behavioral disturbances and emotional disturbances whose onset lies in childhood and youth, e.g., hyperactivity in children, intellectual deficits, in particular, attention disturbances (attention deficit disorders), memory disturbances and cognitive disturbances, e.g., impaired learning and memory (impaired cognitive function), dementia, narcolepsy, and sleep disturbances, e.g., restless leg syndrome; developmental disturbances; anxiety states, delirium, sex-life disturbances, e.g., impotence in men; eating disturbances, e.g., anorexia or bulimia, addiction, and other unspecified disturbances.

The disorders which can be treated in accordance with the invention also include Parkinson's disease and epilepsy, and, in particular, affective disturbances connected thereto.

The addiction diseases include psychic disorders and behavioral disturbances which are caused by the abuse of psychotropic substances, such as pharmaceuticals or narcotics and also other addiction diseases, such as addiction to gaming (impulse control disorders not elsewhere classified). Examples of addictive substances are opioids (e.g., morphine, heroin, and codeine), cocaine, nicotine, alcohol, substances which interact with GABA chloride channel complex, sedatives, hypnotics, and tranquilizers, for example, benzodiazepines; LSD; cannabinoids; psychomotor stimulants, such as 3,4-methylenedioxy-N-methylamphetamine (i.e., ecstasy), amphetamine and amphetamine-like substances, such as methylphenidate and other stimulants including caffeine. Addictive substances of particular consideration are opioids, cocaine, amphetamine or amphetamine-like substances, nicotine, and alcohol.

With regard to the treatment of addiction diseases, particular preference is given to compounds of structural formula (I) and (II) that do not possess a psychotropic effect. This can be observed in a test using rats which, after having been administered a compound of the invention, reduce their self-administration of a psychotropic substance, for example, cocaine.

According to another embodiment of the present invention, the compounds of structural formula (I) and (II) are suitable for treating conditions and diseases whose cause can be at least partially attributed to an anomalous activity of dopamine $D_3$ receptors.

According to another embodiment of the present invention, the treatment is directed toward conditions and diseases that can be influenced by the binding of exogenously administered ligands to dopamine $D_3$ receptors.

The diseases and conditions that can be treated with a compounds of the present invention frequently are characterized by progressive development, i.e., the above-described conditions change over the course of time, and, as a rule, the severity increases and conditions possibly can merge into one another, or other conditions appear in addition to those which already exist can appear.

The compounds according to the invention can be used to treat a large number of signs, symptoms, and/or malfunctions that are connected to disease and condition of the central nervous system and, in particular, the abovementioned diseases and conditions. These signs, symptoms, and/or malfunctions include, for example, a disturbed relationship to reality, lack of insight, and ability to meet customary social norms or the demands made by life, changes in temperament, changes in individual drives, such as hunger, sleep, and thirst, for example, and mood, disturbances in the ability to observe and combine, changes in personality, in particular emotional lability, hallucinations, ego-disturbances, distractedness, ambivalence, autism, depersonalization, and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g., peripheral positional, rotational and oscillatory vertigo, melancholia, hysteria, hypochondria, and the like.

Therefore, compounds of the present invention are suitable for treatment of diseases of the central nervous system, in particular for treating affective disorders; neurotic disturbances, stress disturbances and somatoform disturbances and psychoses and, in particular, for treating schizophrenia and depression. Because of their high selectivity with regard to the $D_3$ receptor, the compounds of structural formula (I) and (II) also are suitable for treating disturbances of kidney function which are caused by diabetes mellitus (see WO 00/67847 incorporated herein by reference) and, especially, diabetic nephropathy.

In the present method, a therapeutically effective amount of one or more compound (I) or (II), as a rule formulated in accordance with pharmaceutical practice, is administered to a human being in need thereof. Whether such a treatment is indicated, depends on the individual case and is subject to medical assessment (diagnosis) that takes into consideration signs, symptoms, and/or malfunctions which are present, the risks of developing particular signs, symptoms and/or malfunctions, and other factors.

A compound of structural formula (I) or (II) can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

The pharmaceutical compositions include those wherein a compound of structural formula (I) or (II) is administered in an effective amount to achieve its intended purpose. Determination of a therapeutically effective amount is well within the capability of those skilled in the art, especially in light of the detailed disclosure provided herein.

The exact formulation, route of administration, and dosage is determined by an individual physician in view of the diagnosed condition or disease. Dosage amount and interval can be adjusted individually to provide levels of a compound of structural formula (I) or (II) that is sufficient to maintain therapeutic effects. The amount of pharmaceutical composition administered is dependent on the subject being treated, on the subject's weight, the severity of the affliction, the manner of administration, and the judgment of the prescribing physician.

Specifically, for administration to a human in the treatment of a disease or condition, oral dosages of a compound of structural formula (I) or (II), individually generally are about 0.005 to about 500 milligrams daily for an average adult patient (70 kg), typically one dose per day or divided into two to three doses per day. Thus, for a typical adult patient, individual doses contain about 0.005 to about 500 milligrams of compound (I) or (II), in a suitable pharmaceutically acceptable vehicle or carrier, for administration in single or multiple doses, once or several times per day. Dosages for intravenous, buccal, or sublingual administration typically are about 0.005 to about 250 milligrams/kg per single dose as required. In practice, the physician determines the actual dosing regimen that is most suitable for an individual patient, and the dosage varies with the age, weight, and response of the particular patient. The above dosages are exemplary of the average case, but there can be individual instances in which higher or lower dosages are merited, and such are within the scope of this invention.

The compounds of the present invention can be administered alone, or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the compounds of structural formula (I) and (II) into preparations that can be used pharmaceutically.

These pharmaceutical compositions can be manufactured in a conventional manner, e.g., by conventional mixing, dissolving, granulating, dragee-making, emulsifying, encapsulating, entrapping, or lyophilizing processes. Proper formulation is dependent upon the route of administration chosen. When a therapeutically effective amount of the compound of structural formula (I) or (II) is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.1% to about 95%, and preferably from about 1% to about 50%, of a compound of structural formula (I) or (II). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I) or (II).

When a therapeutically effective amount of a compound of structural formula (I) or (II) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle. A compound of structural formula (I) or (II) can be infused with other fluids over a 10-30 minute span or over several hours.

Compounds of structural formula (I) and (II) can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the compound of structural formula (I) or (II) to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A compound of structural formula (I) or (II) can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a compound of structural formula (I) or (II) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A compound of structural formula (I) or (II) also can be formulated in rectal compositions, such as suppositories or retention enemas, e.g., containing conventional suppository bases. In addition to the formulations described previously, a compound of structural formula (I) or (II) also can be formulated as a depot preparation. Such long-acting formulations can be administered by implantation (for example, subcutaneously or intramuscularly) or by intramuscular injection. Thus, for example, the compounds of structural formula (I) and (II) can be formulated with suitable polymeric or hydrophobic materials (for example, as an emulsion in an acceptable oil) or ion exchange resins.

In particular, the compounds of structural formula (I) and (II) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The compounds of structural formula (I) and (II) also can be injected parenterally, for example, intravenously, intramuscularly, subcutaneously, or intracoronarily. For parenteral administration, the endothelin antagonists are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one embodiment, the kit includes a compound or composition described herein as useful for practice of a method (e.g., a composition comprising a compound of structural formula (I) or (II) and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

As discussed above, although potent and selective dopamine $D_3$ receptor ligands based upon in vitro binding data have been reported, ligands that are highly active and selective in vivo at the $D_3$ receptor are still lacking Several prior $D_3$ ligands also possessed physical properties, e.g., a low water solubility, that hindered development as therapeutic agents.

In accordance with an important feature of the present invention, compounds of structural formula (I) and (II) were synthesized and evaluated as ligands for the dopamine 3 ($D_3$) receptor. For example, compound 38 described below has a $K_i$ value of 0.73 nM to $D_3$ and a selectivity of about 13,700 and about 500-fold over the $D_1$-like and $D_2$ receptors, respectively. Compound 52 described below has a $K_i$ value of 0.38 nM to $D_3$ and a selectivity of about 46,000 and about 450 over the $D_1$-like and $D_2$ receptors, respectively.

Synthesis of Compounds

Compounds of the present invention were prepared as follows.

Solvents and reagents were obtained commercially and used without further purification. Reactions were monitored by TLC carried performed on 250 μm E. Merck silica gel plates (60F-254) using UV light as a visualizing agent. E. Merck silica gel (60, particle size 15-40 μm) was used for flash column chromatography. NMR spectra were recorded on a Bruker Avance300 spectrometer (300 MHz). Chemical shifts (6) are reported as δ values (ppm) downfield relative to TMS as an internal standard, with multiplicities reported in the usual manner. Low resolution mass spectra were obtained from high resolution electrospray ionization mass spectra (MS) were run on a Micromass AutoSpec Ultima mass spectrometer. Elemental analysis (EA) was performed using a Perkin-Elmer 2400 Series II Analyzer. HPLC analysis was performed on a Waters 2795 using a Waters SunFire C18 (150 mm×4.6 mm) column, mobile phase flow 1.0 mL/min, gradient water (with 0.1% TFA)/acetonitrile (with 0.1% TFA) 0 to about 50%, and UV detection at 254 nm.

The synthesis of the present compounds is provided in Schemes 1-3. Basically, pramipexole 9 was reacted with commercially available tert-butyl trans-4-(2-oxoethyl)cyclohexylcarbamate to give intermediate 13. Intermediate 13 was treated with trifluoroacetic acid (TFA) to afford amine 14.

Scheme 1. Synthesis of compounds.

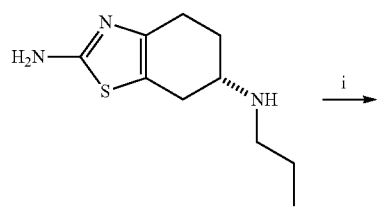

9

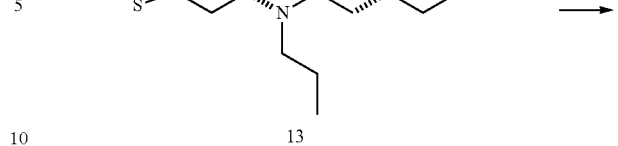

13

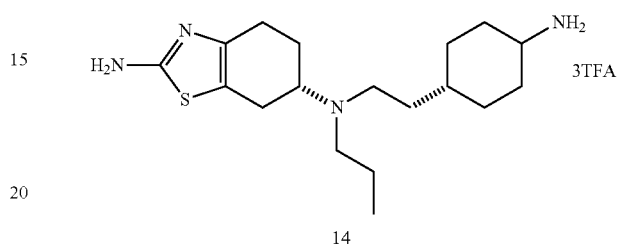

14

Conditions and reagents: (i) tert-butyl trans-4-(2-oxoethyl)cyclohexylcarbamate, NaBH(OAc)₃, HAc, DCM; (ii) TFA, DCM, RT, 12 h.

The synthesis of compounds 33-38 is straightforward and is provided in Scheme 2. Briefly, compound 14 was condensed with the appropriate carboxylic acid ($RCO_2H$) to give compounds 33-38.

Scheme 2. Synthesis of compounds 33-38.

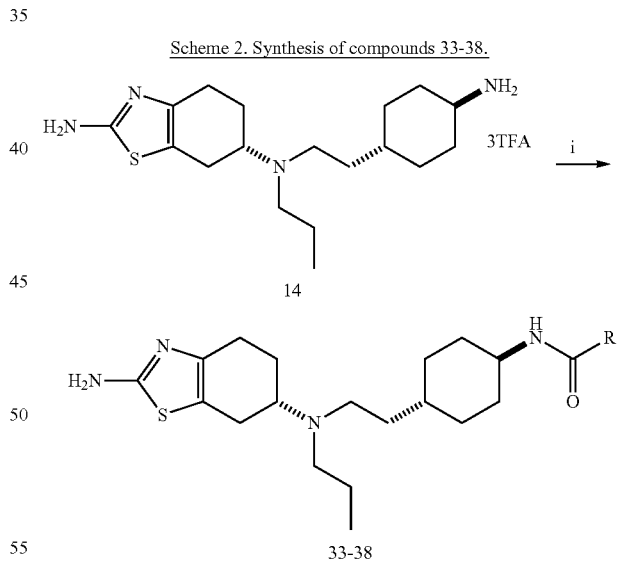

Conditions and reagents: (i) RCO₂H, EDCI, HOBt, DIPEA, DCM

The synthesis of compounds 43-47 and 51-53 is straightforward and is provided in Scheme 3. Compound 14 was reacted with the appropriate sulfonyl chloride ($RSO_2Cl$) in the presence of diisopropylethylamine (DIPEA) to give compounds 43-47 and 51-53.

Scheme 3. Synthesis of compounds 43-47 and 51-53.

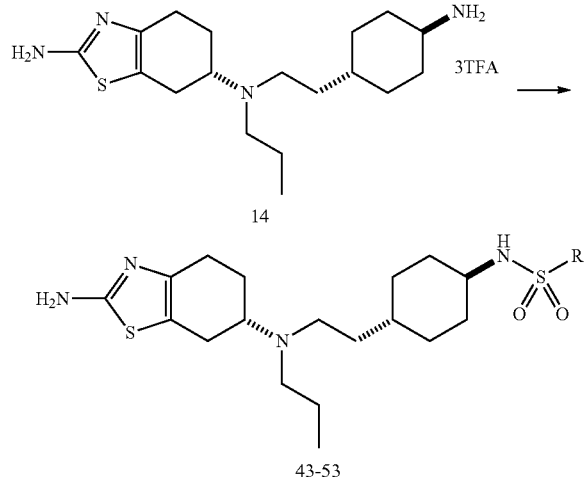

Conditions and reagents: (i) RSO₂Cl, DIPEA, DCM, RT, 2 h

Trans-N-(4-2-(((s)-2-amino-4,5,6,7-tetrahydrobenzo[d]thiazol-6-yl)(propyl)amino)ethyl)cyclohexyl)carbamate (13)

Tert-butyl trans-4-(2-oxoethyl)cyclohexylcarbamate (114 mg, 0.47 mmol), acetic acid (HAc) (57 mg, 0.95 mmol) and sodium triacetoxyborohydride (NaBH(OAc)₃ (200 mg, 0.95 mmol) were added to a solution of pramipexole (100 mg, 0.47 mmol) in dichloroethane (20 mL) and the reaction mixture was stirred at room temperature (RT) for 6 hr. The reaction was quenched with water and the pH was adjusted to 9-10 by addition of aqueous sodium carbonate solution. Then, the mixture was extracted with dichloromethane (DCM) for 3 times. The organic lawyer was separated, combined, and evaporated. The residue was chromatographed (SiO₂, ethyl acetate:methanol=95:5) to give compound 13 as a colorless oil (155 mg, 75%).

$^1$H NMR (CDCl₃, 300 MHz) δ 4.70 (s, 2H), 4.50-4.30 (m, 1H), 3.50-3.25 (m, 1H), 3.10-2.90 (m, 1H), 2.75-2.25 (m, 8H), 2.00-1.55 (m, 7H), 1.44 (s, 9H), 1.42-0.98 (m, 8H), 0.87 (t, J=7.3 Hz, 3H).

(s)-N⁶-(2-((1r,4s)-4-aminocyclohexyl)ethyl)-N⁶-propyl-4,5,6,7-tetrahydrobenzo[d]thiazole-2,6-diamine (14)

TFA (2 mL) was added to a solution of compound 13 in dichloromethane (10 mL) and the mixture was stirred at room temperature for 12 hr. Solvent and TFA were removed under vacuum and the residue was used directly for the next step without further purification.

General Procedure for the Synthesis of Compounds 33-38.

Appropriate carboxylic acid (0.1 mmol), EDCI (1-(3-dimethylaminopropyl)-3-ethylcarbodiimide hydrochloride) (19 mg, 0.1 mmol), HOBt (1-hydroxybenzotriazole) (14 mg, 0.1 mmol), and diisopropylethylamine (52 mg, 0.4 mmol) were added to a suspension of 14 (68 mg, 0.1 mmol) in dichloromethane (10 mL) and the mixture was stirred at room temperature for 6 hr. The reaction was quenched with water and the pH was adjusted to 9-10 by addition of aqueous sodium carbonate. The mixture was extracted with dichloromethane for 3 times. The organic lawyer was separated, combined, and evaporated. The residue was chromatographed (SiO₂, ethyl acetate:methanol=95:5) to give compounds 33-38.

Trans-N-(4-2-(((s)-2-amino-4,5,6,7-tetrahydrobenzo[d]thiazol-6-yl)(propyl)amino)ethylcyclohexyl)-4-(5-methyl-1,2,4-oxadiazol-3-yl)benzamide (33)

$^1$H NMR (CDCl₃, 400 MHz) δ 8.11 (d, J=8.4 Hz, 2H), 7.85 (d, J=8.4 Hz, 2H), 6.13 (d, J=6.4 Hz, 1H), 4.94 (s, 2H), 4.00-3.88 (m, 1H), 3.07-2.97 (m, 1H), 2.78-2.40 (m, 8H), 2.70 (s, 3H), 2.20-1.62 (m, 6H), 1.54-1.05 (m, 9H), 0.87 (t, J=8.0 Hz, 3H); $^{13}$C NMR (CDCl₃, 100 MHz) δ 176.88, 167.73, 165.97, 165.68, 145.08, 137.31, 129.39, 127.47, 127.44, 117.39, 57.40, 52.65, 49.38, 48.50, 36.09, 35.17, 33.12, 31.94, 26.61, 25.86, 24.94, 22.27, 12.37, 11.87; MS m/z [M+H]⁺ 523.8; purity HPLC 99.3%, $t_R$=5.58 min.

Trans-N-(4-2-(((s)-2-amino-4,5,6,7-tetrahydrobenzo[d]thiazol-6-yl)(propyl)amino)ethylcyclohexyl)-4-(5-ethyl-1,2,4-oxadiazol-3-yl)benzamide (34) $^1$H NMR (CDCl₃, 400 MHz) δ 8.09 (d, J=8.4 Hz, 2H), 7.84 (d, J=8.4 Hz, 2H), 6.27 (d, J=8.0 Hz, 1H), 5.29 (s, 2H), 3.96-3.83 (m, 1H), 3.04-2.94 (m, 3H), 2.78-2.40 (m, 8H), 2.18-1.62 (m, 6H), 1.50-1.02 (m, 12H), 0.86 (t, J=8.0 Hz, 3H); $^{13}$C NMR (CDCl₃, 100 MHz) δ 181.07, 167.59, 166.06, 144.77, 137.23, 129.51, 127.49, 127.44, 117.01, 57.40, 52.63, 49.39, 48.50, 35.98, 35.17, 33.07, 31.94, 26.47, 25.79, 24.86, 22.19, 20.31, 11.87, 10.79; MS m/z [M+H]⁺ 537.8; purity HPLC 98.7%, tR=3.43 min. 98.0%, $t_R$=3.87 min.

Trans-N-(4-2-(((s)-2-amino-4,5,6,7-tetrahydrobenzo[d]thiazol-6-yl)(propyl)amino)ethylcyclohexyl)-3-(5-methyl-1,2,4-oxadiazol-3-yl)benzamide (38) $^1$H NMR (CDCl₃, 400 MHz) δ 8.33 (s, 1H), 8.15 (d, J=8.0 Hz, 1H), 7.97 (d, J=8.0 Hz, 1H), 7.53 (t, J=8.0 Hz, 1H), 6.29 (d, J=8.0 Hz, 1H), 5.36 (s, 2H), 3.98-3.84 (m, 1H), 3.09-2.98 (m, 1H), 2.78-2.40 (m, 8H), 2.66 (s, 3H), 2.17-1.60 (m, 6H), 1.54-1.02 (m, 9H), 0.86 (t, J=8.0 Hz, 3H); $^{13}$C NMR (CDCl₃, 100 MHz) δ 176.91, 167.81, 166.74, 165.87, 144.05, 135.74, 130.37, 129.96, 129.32, 126.93, 125.03, 116.36, 57.44, 52.57, 49.36, 48.52, 35.63, 35.23, 33.02, 31.95, 26.12, 25.57, 24.78, 21.90, 12.39, 11.86; MS m/z [M+H]⁺ 523.7; purity HPLC 95.1%, $t_R$=4.18 min.

General Procedure for the Synthesis of Compounds 43-47 and 51-53.

Diisopropylethylamine (52 mg, 0.4 mmol) and appropriate sulfonyl chloride (0.12 mmol) were added to a suspension of compound 14 (68 mg, 0.1 mmol) in dichloromethane (10 mL) and the mixture was stirred at room temperature for 2 hr. The reaction was quenched with water and the pH was adjusted to 9-10 by addition of aqueous sodium carbonate. The mixture was extracted with dichloromethane for 3 times. The organic lawyer was separated, combined, and evaporated. The residue was chromatographed (SiO₂, ethyl acetate:methanol=95:5) to give compounds 43-47 and 51-53.

Trans-N-(4-2-(((s)-2-amino-4,5,6,7-tetrahydrobenzo[d]thiazol-6-yl)(propyl)amino)ethylcyclohexyl)-3-fluorobenzenesulfonamide (43)

$^1$H NMR (CDCl₃, 400 MHz) δ 7.69 (d, J=7.6 Hz, 1H), 7.60 (d, J=8.4 Hz, 1H), 7.52-7.46 (m, 1H), 7.29-7.24 (m, 1H), 5.31 (s, 1H), 5.09 (s, 2H), 3.18-2.98 (m, 2H), 2.76-2.38 (m, 8H), 1.99-1.62 (m, 6H), 1.50-0.84 (m, 9H), 0.86 (t, J=7.2 Hz, 3H); $^{13}$C NMR (CDCl₃, 100 MHz) δ 166.11, 162.29 (d, $J_{F-C}$=248.6 Hz), 144.81, 143.75, 130.84 (d, $J_{F-C}$=7.3 Hz), 122.59 (d, $J_{F-C}$=3.7 Hz), 119.55 (d, $J_{F-C}$=21.1 Hz), 117.02, 114.24 (d, $J_{F-C}$=24.8 Hz), 57.34, 53.39, 52.58, 48.34, 35.65, 34.53, 33.90, 31.92, 29.67, 25.94, 24.62, 22.09, 11.83; MS m/z [M+H]$^+$ 495.8; purity HPLC 95.6%, $t_R$=3.97 min.

Trans-N-(4-2-(((s)-2-amino-4,5,6,7-tetrahydrobenzo[d]thiazol-6-yl)(propyl)amino)ethylcyclohexyl)-4-methoxybenzenesulfonamide (44)

$^1$H NMR (CDCl$_3$, 400 MHz) δ 7.82 (d, J=8.8 Hz, 2H), 6.95 (d, J=8.8 Hz, 2H), 5.21 (d, J=6.0 Hz, 1H), 5.13 (s, 2H), 3.89 (s, 3H), 3.05-2.96 (m, 2H), 2.78-2.35 (m, 8H), 1.97-1.61 (m, 6H), 1.57-0.85 (m, 9H), 0.86 (t, J=7.6 Hz, 3H); $^{13}$C NMR (CDCl$_3$, 100 MHz) δ166.02, 162.63, 144.85, 133.24, 129.01, 117.04, 114.15, 57.38, 55.59, 53.11, 52.58, 48.38, 35.74, 34.61, 33.91, 31.99, 26.62, 25.91, 24.71, 22.11, 11.83; MS m/z [M+H]$^+$ 507.7; purity HPLC 95.6%, $t_R$=4.40 min.

Trans-N-(4-2-(((s)-2-amino-4,5,6,7-tetrahydrobenzo[d]thiazol-6-yl)(propyl)amino)ethylcyclohexyl)-3-chlorobenzenesulfonamide (45)

$^1$H NMR (CDCl$_3$, 400 MHz) δ 7.89 (s, 1H), 7.78 (d, J=7.6 Hz, 1H), 7.56-7.42 (m, 2H), 5.67 (s, 1H), 5.10 (s, 2H), 3.18-2.95 (m, 2H), 2.75-2.37 (m, 8H), 1.96-1.60 (m, 6H), 1.54-0.84 (m, 9H), 0.87 (t, J=8.0 Hz, 3H); $^{13}$C NMR (CDCl$_3$, 100 MHz) δ 166.14, 144.83, 143.60, 135.11, 132.45, 130.35, 126.96, 124.93, 117.13, 57.26, 53.41, 52.57, 48.28, 35.80, 34.50, 33.94, 31.99, 26.72, 26.07, 24.61, 22.22, 11.85; MS m/z [M+H]$^+$ 511.5; purity HPLC 99.6%, $t_R$=4.26 min.

Trans-N-(4-2-(((s)-2-amino-4,5,6,7-tetrahydrobenzo[d]thiazol-6-yl)(propyl)amino)ethylcyclohexyl)-4-chlorobenzenesulfonamide (46)

$^1$H NMR (CDCl$_3$, 400 MHz) δ 7.83 (d, J=8.8 Hz, 2H), 7.47 (d, J=8.8 Hz, 2H), 5.52 (s, 1H), 5.06 (s, 2H), 3.15-2.96 (m, 2H), 2.78-2.37 (m, 8H), 2.00-1.61 (m, 6H), 1.54-0.84 (m, 9H), 0.86 (t, J=8.0 Hz, 3H); $^{13}$C NMR (CDCl$_3$, 100 MHz) δ 166.19, 144.83, 140.38, 138.68, 129.29, 128.35, 117.07, 57.23, 53.33, 52.55, 48.24, 35.82, 34.47, 33.91, 32.02, 26.75, 26.12, 24.56, 22.25, 11.85; MS m/z [M+H]$^+$ 511.5; purity HPLC 99.7%, $t_R$=4.27 min.

Trans-N-(4-2-(((s)-2-amino-4,5,6,7-tetrahydrobenzo[d]thiazol-6-yl)(propyl)amino)ethylcyclohexyl)-2-chlorobenzenesulfonamide (47)

$^1$H NMR (CDCl$_3$, 400 MHz) δ 8.13 (dd, J=1.2, 7.2 Hz, 1H), 7.58-7.40 (m, 3H), 4.99 (d, J=7.2 Hz, 1H), 4.85 (s, 2H), 3.15-2.96 (m, 2H), 2.78-2.37 (m, 8H), 2.00-1.60 (m, 6H), 1.54-0.82 (m, 9H), 0.86 (t, J=8.0 Hz, 3H); $^{13}$C NMR (CDCl$_3$, 100 MHz) δ 165.57, 145.06, 138.67, 133.49, 131.58, 131.32, 130.93, 127.25, 117.46, 57.33, 53.62, 52.60, 48.35, 35.86, 34.59, 33.69, 31.80, 26.58, 25.83, 24.86, 22.25, 11.84; MS m/z [M+H]$^+$ 511.7; purity HPLC 97.5%, $t_R$=4.25 min.

Trans-N-(4-2-(((s)-2-amino-4,5,6,7-tetrahydrobenzo[d]thiazol-6-yl)(propyl)amino)ethylcyclohexyl)-6-chloropyridine-3-sulfonamide (51)

$^1$H NMR (CDCl$_3$, 400 MHz) δ 8.88 (d, J=2.0 Hz, 1H), 8.12 (dd, J=2.0, 8.4 Hz, 1H), 7.48 (d, J=8.4 Hz, 1H), 5.70 (s, 1H), 4.93 (s, 2H), 3.25-2.95 (m, 2H), 2.75-2.40 (m, 8H), 2.00-1.62 (m, 6H), 1.50-0.82 (m, 9H), 0.86 (t, J=8.0 Hz, 3H); $^{13}$C NMR (CDCl$_3$, 100 MHz) δ 165.84, 155.11, 148.24, 144.94, 137.51, 137.11, 124.65, 117.37, 57.21, 53.59, 52.54, 48.18, 34.39, 34.08, 34.04, 31.68, 26.74, 26.13, 24.51, 22.21, 11.83; MS m/z [M+H]$^+$ 512.7; purity HPLC 98.7%, $t_R$=4.05 min.

Trans-N-(4-2-(((s)-2-amino-4,5,6,7-tetrahydrobenzo[d]thiazol-6-yl)(propyl)amino)ethylcyclohexyl)-2-chloropyridine-3-sulfonamide (52)

$^1$H NMR (CDCl$_3$, 400 MHz) δ 8.60-8.40 (m, 2H), 7.43 (dd, J=4.8, 8.0 Hz, 1H), 5.82 (s, 1H), 5.10 (s, 2H), 3.18-2.94 (m, 2H), 2.75-2.35 (m, 8H), 1.96-1.60 (m, 6H), 1.44-0.82 (m, 9H), 0.86 (t, J=8.0 Hz, 3H); $^{13}$C NMR (CDCl$_3$, 100 MHz) δ 165.96, 152.23, 147.83, 144.90, 139.72, 136.32, 122.80, 117.06, 57.28, 53.79, 52.55, 48.26, 35.76, 34.44, 33.72, 31.86, 26.66, 25.93, 24.69, 22.19, 11.83; MS m/z [M+H]$^+$ 512.6; purity HPLC 96.7%, $t_R$=3.97 min.

Trans-N-(4-2-(((s)-2-amino-4,5,6,7-tetrahydrobenzo[d]thiazol-6-yl)(propyl)amino)ethylcyclohexyl)-4-chloropyridine-3-sulfonamide (53)

$^1$H NMR (CDCl$_3$, 400 MHz) δ 9.20 (s, 1H), 8.67 (d, J=5.2 Hz, 1H), 7.48 (d, J=5.2 Hz, 1H), 5.80 (s, 1H), 5.11 (s, 2H), 3.18-2.94 (m, 2H), 2.75-2.35 (m, 8H), 1.96-1.62 (m, 6H), 1.47-0.84 (m, 9H), 0.87 (t, J=8.0 Hz, 3H); $^{13}$C NMR (CDCl$_3$, 100 MHz) δ 165.97, 153.69, 150.88, 144.89, 141.95, 135.37, 126.05, 117.09, 57.27, 53.69, 52.56, 48.25, 35.74, 34.47, 33.79, 31.84, 26.66, 25.97, 24.69, 22.22, 11.84; MS m/z [M+H]$^+$ 512.6; purity HPLC 95.7%, $t_R$=4.12 min.

Compounds having an affinity for the dopamine D$_3$ receptor have been disclosed, for example, in WO 95/04713, WO 96/23760, WO 97/45503, WO 98/27081, WO 99/58499, WO 05/118588, WO 06/040182, WO 06/082456, WO 06/066885, and WO 08/026,046. Some of these compounds possess moderate affinities and/or selectivities for the dopamine D$_3$ receptor, and therefore have been proposed as suitable for treating diseases of the central nervous system. Unfortunately, the affinity and selectivity of these compounds towards the D$_3$ receptor and/or their pharmacological profile are not satisfactory. In addition, although several promising D$_3$ ligands showed excellent in vitro potency and selectivity, the compounds did not perform well in in vivo functional assays. Consequently, there is an ongoing need to provide new compounds that have a high affinity for the D$_3$ receptor and an improved selectivity. The compounds also should have a good pharmacological profile, e.g., a high brain plasma ratio, a high bioavailability, a good metabolic stability, and/or a decreased inhibition of the mitochondrial respiration.

Through extensive chemical modifications to previously reported D$_3$ ligands, D$_3$ ligands with high binding affinities to the D$_3$ receptor and an excellent selectivity over the D$_2$ and D$_1$ receptors based upon in vitro binding data have been discovered. Compounds 38 and 52 are potent and selective D$_3$ ligands. Both compounds bind to D$_3$ with a K$_i$ value of less than 1 nM and display a selectivity of 450-494 times over D$_2$ and a greater than 10,000 selectivity over D$_1$. Most importantly, in vivo functional experiments demonstrate that compounds 38 and 52 function as highly active D$_3$ partial agonists and display an outstanding selectivity at the D$_3$ receptor over the D$_2$ receptor.

While both compounds are active as D$_3$ partial agonists at doses as low as 0.0032 mg/kg in the yawning assay in rats, the compounds show no activity at the D$_2$ receptors at concentrations as high as 3.2 mg/kg, thereby displaying over 1000-fold selectivity for D$_3$ over D$_2$. Evaluations of their interactions with pramipexole, a known D$_3$ and D$_2$ full agonist with a narrow range of D$_3$ selectivity, confirm D$_3$ partial agonist activity of compounds 38 and 52 and a devoid D$_2$ activity at 3.2 mg/kg. Compounds 38 and 52 are the most active and selective D$_3$ partial agonists reported to date based upon in vivo functional assays. Compounds 38 and 50 also are very soluble in water (greater than 100 mg/ml), making them ideal pharmacological tools to further investigate the role of the $D_3$ receptor in drug abuse and other neurological conditions in animal models. Compounds of the present invention therefore have therapeutic potential for the treatment of drug abuse and other neurological conditions in which the $D_3$ receptor plays a role.

Compounds 10 and 11 were previously reported.[25] Due to discontinuation of $D_3$ radioligand [$^3$H]PD128907, compounds 10 and 11 were re-evaluated in both the $D_3$ and $D_2$ assays using $D_3$ radioligand [$^3$H]—R(+)-7-hydroxy-N,N-di-n-propyl-2-aminotetralin ([$^3$H]—R(+)-7-OH-DPAT). Compounds 10 and 11 were found to bind to $D_3$ with $K_i$ values of 1.0±0.04 nM and 1.1±0.3 nM, respectively, compared to 0.41±0.031 nM and 0.40±0.057 nM, respectively, as previously reported.[25] Compounds 10 and 11 bind to $D_2$ with $K_i$ values of 239±60 nM and 185±61 nM, respectively, compared to 330±69 nM and 307±38 nM, respectively, as previously reported.[25] Due to primarily the 2.5-fold increase in $K_i$ values in the $D_3$ receptor binding assay, the selectivity of compounds 10 and 11 for $D_3$ over $D_2$ has decreased to 239- and 168-times, respectively, compared to 800- and 763-times, respectively, as previously reported.[25]

The binding affinities at the $D_1$-like, $D_2$-like, and $D_3$ receptors of compounds of structural formula (I) were tested. The results are summarized in Table 1.

TABLE 1

Binding Affinities at the $D_1$-like, $D_2$-like, and $D_3$ Receptors in Binding Assays Using Rat Brain.

| ligand | R | $D_3$ ([$^3$H]-R(+)-7-OH-DPAT) | $D_2$-like ([$^3$H]Spiperone) | $D_1$-like ([$^3$H]SCH23390) | $D_2$-like/$D_3$ | $D_1$-like/$D_3$ |
|---|---|---|---|---|---|---|
| 11 | naphthalen-2-yl | 1.1 ± 0.3 | 185 ± 61 | NT | 168 | NT |
| 33 | 4-(5-methyl-1,2,4-oxadiazol-3-yl)phenyl | 1.3 ± 0.12 | 442 ± 41 | 34,613 ± 3,625 | 345 | 27,041 |
| 34 | 4-(5-ethyl-1,2,4-oxadiazol-3-yl)phenyl | 2.1 ± 0.15 | 328 ± 53 | 17,748 ± 921 | 155 | 8,381 |
| 35 | 4-(5-isopropyl-1,2,4-oxadiazol-3-yl)phenyl | 2.0 ± 0.19 | 470 ± 53 | 10,912 ± 756 | 231 | 5,366 |

TABLE 1-continued

Binding Affinities at the $D_1$-like, $D_2$-like, and $D_3$ Receptors in Binding Assays Using Rat Brain.

| ligand | R | $K_i \pm$ SEM (nM) | | | Selectivity | |
|---|---|---|---|---|---|---|
| | | $D_3$ ([$^3$H]-R(+)-7-OH-DPAT) | $D_2$-like ([$^3$H]Spiperone) | $D_1$-like ([$^3$H]SCH23390) | $D_2$-like/$D_3$ | $D_1$-like/$D_3$ |
| 36 | | $3.5 \pm 0.57$ | $633 \pm 100$ | $11,410 \pm 765$ | 180 | 3,245 |
| 37 | | $1.5 \pm 0.23$ | $491 \pm 70$ | $5,000 \pm 495$ | 339 | 3,448 |
| 38 | | $0.73 \pm 0.028$ | $359 \pm 58$ | $9,937 \pm 888$ | 494 | 13,678 |

Compound 33 contains a 4-(5-methyl-1,2,4-oxadiazol-3-yl)phenyl group (Table 1). Compound 33 binds to $D_3$ with the same high affinity ($K_i$=1.3 nM) as compound 11, but its selectivity over the $D_2$ receptor is improved to 345-fold due to decreased binding affinity to $D_2$. Compounds 34-38 contain different 1,2,4-oxadiazol-3-yl-phenyl groups (Table 1). Replacement of the methyl group in compound 33 with ethyl (34), isopropyl (35), or cyclopropyl (36) decreases the binding affinity to $D_3$ by 2-3 times and also the selectivity for $D_3$ over $D_2$ by 2-3 times as compared to compound 33. Compounds 37 and 38, in which the 4-(5-methyl-1,2,4-oxadiazol-3-yl)phenyl group in compound 33 is replaced by a 3-(5-ethyl-1,2,4-oxadiazol-3-yl)phenyl or a 3-(5-methyl-1,2,4-oxadiazol-3-yl)phenyl, bind to $D_3$ with $K_i$ values of 1.5 nM and 0.73 nM, respectively. Their selectivity for $D_3$ over $D_2$ is 339 and 494, respectively.

The binding affinities at the $D_1$-like, $D_2$-like, and $D_3$ receptors of compounds of structural formula (II) also were tested. The results are summarized in Table 2. Compounds 43-47 and 51-53 each contain a sulfonamide group in place of the amide group in the linker region (Table 2).

TABLE 2
Binding Affinities at the $D_1$-like, $D_2$-like, and $D_3$ Receptors in Binding Assays Using Rat Brain.
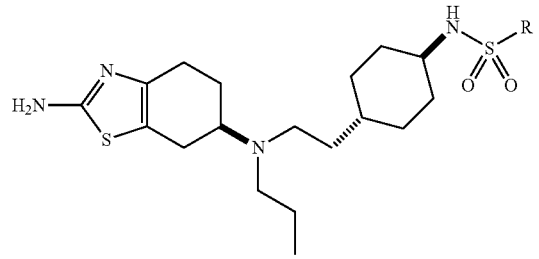
| ligand | R | $K_i \pm$ SEM (nM) | | | Selectivity | |
|---|---|---|---|---|---|---|
| | | $D_3$ ([$^3$H]-R(+)-7-OH-DPAT) | $D_2$-like ([$^3$H] Spiperone) | $D_1$-like ([$^3$H] SCH23390) | $D_2$-like/$D_3$ | $D_1$-like/$D_3$ |
| 43 | 3-F-phenyl | 0.72 ± 0.11 | 136 ± 17 | 10,359 ± 805 | 190 | 14,467 |
| 44 | 4-OMe-phenyl | 0.78 ± 0.11 | 38 ± 3 | 21,330 ± 1,006 | 49 | 27,487 |
| 45 | 3-Cl-phenyl | 1.1 ± 0.1 | 127 ± 15 | 5,552 ± 231 | 117 | 5,094 |
| 46 | 4-Cl-phenyl | 0.95 ± 0.01 | 71 ± 5 | 8,287 ± 257 | 75 | 8,754 |
| 47 | 2-Cl-phenyl | 0.68 ± 0.06 | 66 ± 11 | 9,484 ± 630 | 98 | 14,015 |
| 51 | 2-Cl-pyridin-5-yl | 0.63 ± 0.04 | 28 ± 3 | 8,191 ± 937 | 44 | 12,933 |
| 52 | 2-Cl-pyridin-3-yl | 0.38 ± 0.05 | 170 ± 19 | 17,443 ± 1,727 | 451 | 46,310 |

TABLE 2-continued

Binding Affinities at the $D_1$-like, $D_2$-like, and $D_3$ Receptors in Binding Assays Using Rat Brain.

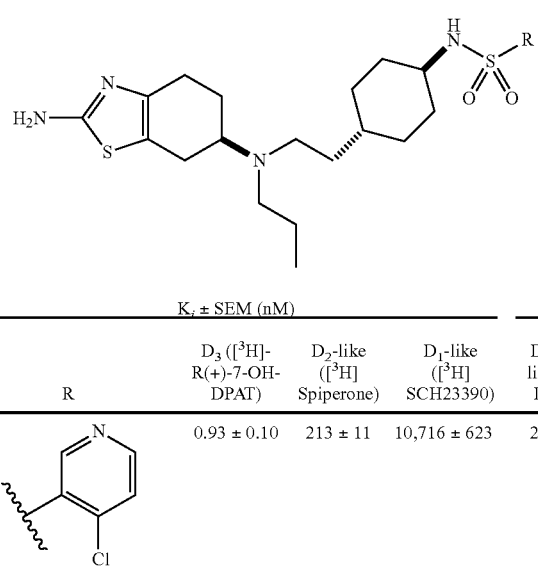

| | | $K_i \pm$ SEM (nM) | | | Selectivity | |
|---|---|---|---|---|---|---|
| ligand | R | $D_3$ ([$^3$H]-R(+)-7-OH-DPAT) | $D_2$-like ([$^3$H] Spiperone) | $D_1$-like ([$^3$H] SCH23390) | $D_2$-like/$D_3$ | $D_1$-like/$D_3$ |
| 53 | | $0.93 \pm 0.10$ | $213 \pm 11$ | $10,716 \pm 623$ | 229 | 11,523 |

Present compounds 43-47 and 51-53 illustrate the effect of different substituents on the phenyl ring of the $R^2$ group of structural formula (II) on binding and selectivity. Compound 43, which has a meta-fluoro substituent, has a high binding affinity to $D_3$=0.72 nM) and displays 190-fold selectivity over $D_2$. Compound 44, which has a methoxy group at the para-position of the phenyl ring, also binds to $D_3$ with a high affinity ($K_i$=0.78 nM), but its selectivity over $D_2$ is decreased to 49-fold due to its increased binding affinity to $D_2$. Compounds 45-47 with a chloro substituent at three different positions on the phenyl ring have high binding affinities (0.68-1.1 nM) to $D_3$ and also approximately 100-fold selectivity over $D_2$.

Table 2 illustrates the effect of replacing one carbon atom in the phenyl ring with a nitrogen atom. Compound 51, in which a nitrogen atom is at the meta-position of the phenyl ring in compound 46, binds to $D_3$ with the same affinity as compound 46 but is slightly less selective than Compound 46 over $D_2$. Compound 52, in which a nitrogen atom was inserted into the ortho-position with respect to the chloro substituent in the phenyl ring in compound 47, binds to $D_3$ with a $K_i$ value of 0.38 nM and has a selectivity of 451 times over $D_2$. Compound 53, in which a nitrogen atom was inserted into the para-position with respect to the chloro substituent in the phenyl ring in 47, binds to $D_3$ with a $K_i$ value of 0.93 nM and has a selectivity of 229 times over $D_2$.

The present compounds therefore have very high affinities to $D_3$ and an excellent selectivity over $D_2$. Among them, compound 38 (UM-206) and compound 52 (UM-226) bind to $D_3$ with $K_i$ values of 0.73 nM and 0.38 nM, respectively, and have a selectivity of 494 and 451 times, respectively, over $D_2$. These two compounds also display a selectivity of greater than 10,000 times for $D_3$ over the $D_1$-like receptors.

In Vivo Functional Evaluations in Rats

Despite very high affinities to $D_3$, compounds 10 and 11 were found to be only active at very high doses in in vivo functional assays in rats, thereby suggesting a potentially low bioavailability in the brain. Compounds 38 and 52 therefore were evaluated for in vivo activity and selectivity at the $D_3$ receptor.

Figure 2:
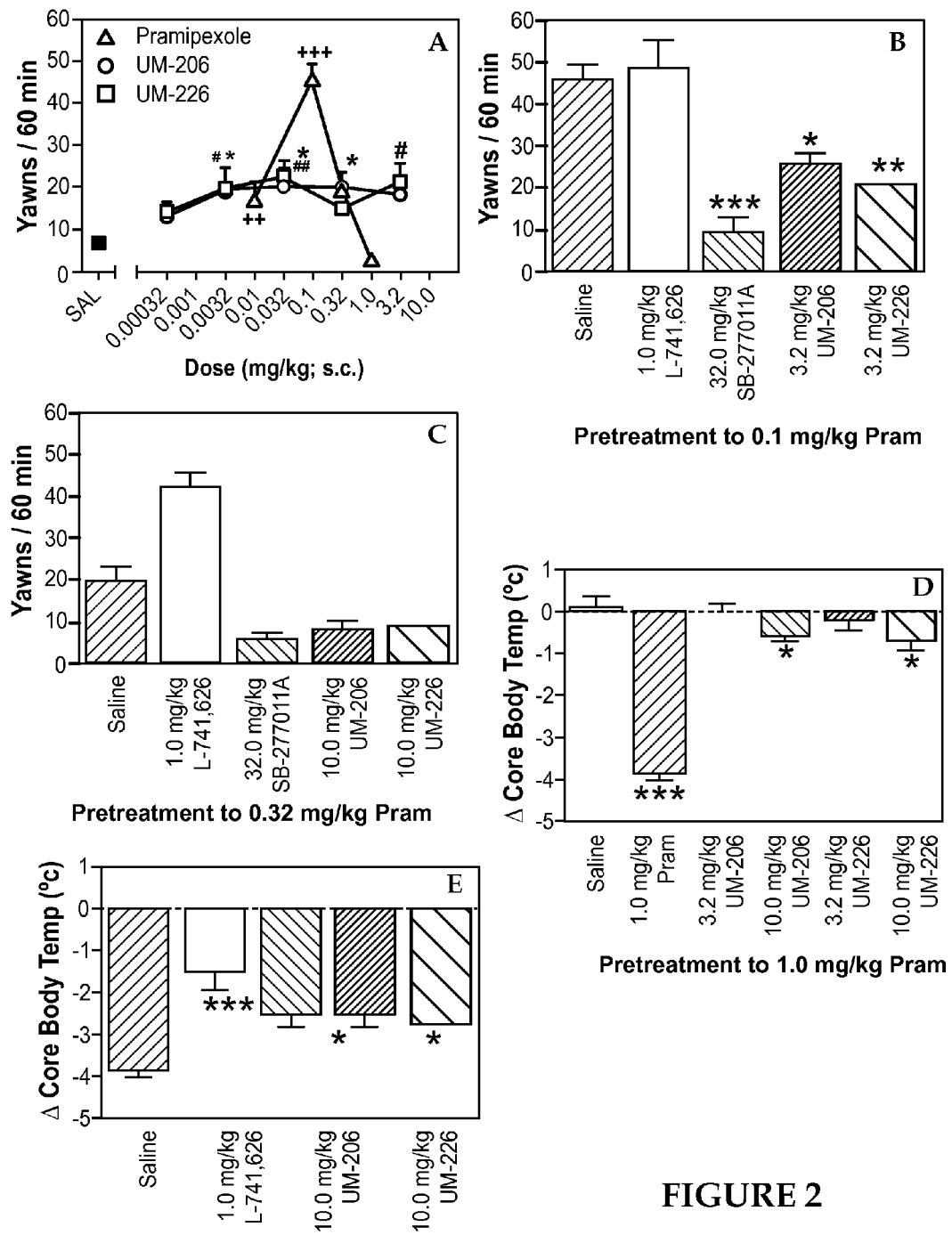
FIG. 2 contains graphs illustrating yawns/60 minutes (A-C) and change in core body temperature (D and E) for rats treated with pramipexole (compound 9), UM-206 (compound 38), and UM-226 (compound 52).

FIG. 2 summarizes functional evaluations of the $D_3$ and $D_2$ activity of pramipexole (compound 9) and UM-206 (compound 38) and UM-226 (compound 52) in yawning and hypothermia assays in rats. One-way, repeated-measures ANOVA with post-hoc Newman-Keuls tests were used to determine whether the compounds induced significantly more yawning or hypothermia compared to a vehicle, as well as to determine if pretreatments significantly altered pramiepxole-induced yawning or hypothermia (*, $p<0.05$; $p<0.01$; *$p<0.001$).

Considerable evidence suggests that yawning provides a sensitive measure of agonist activity of a ligand at the dopamine $D_3$ receptor,[34] whereas the hypothermic effects are mediated by the agonist activity at the $D_2$ receptor.[30,35,36] Accordingly, compounds 38 and 52 were evaluated for the effect in the induction of yawning and hypothermia in rats, respectively. Pramipexole, a full agonist at both the $D_3$ and $D_2$ receptors, was included in the test as the control compound. Similar to previous reports[25,30,31,33-36], pramipexole produced dose-dependent increases in yawning over low doses (0.032 and 0.1 mg/kg), with decreased yawning at 0.32 and 1 mg/kg and the induction of hypothermia at 1 mg/kg (FIGS. 2A and 2D), consistent with its full agonist activity at the $D_3$ and $D_2$ receptors and its narrow in vivo selectivity for $D_3$ over $D_2$.

In contrast to pramipexole, which produced large increase in yawning over a relatively narrow range of doses, compounds 38 and 52 induced low levels of yawning over a wide range of doses, with significant increases observed at doses as low as 0.0032 mg/kg that persisted until a dose of at least 3.2 mg/kg. The increases in yawning induced by both compound 38 and compound 52 at doses between 0.0032 and 3.2 mg/kg are at 25% of the maximum effect achieved by pramipexole at 0.1 mg/kg.

Significantly, both compounds 38 and 52 produced no significant decreases in body temperature at a dose of 3.2 mg/kg. Although both compound 38 and compound 52 had a significant effect in induction of hypothermia at 10.0 mg/kg, these changes were much smaller in magnitude than those observed with pramipexole. Together, the data suggests that 38 and 52 are (a) highly bioavailable, (b) readily cross the blood-brain barrier, (c) function as low efficacy agonists at doses of 0.0032-3.2 mg/kg at the $D_3$ receptor, and (d) have no activity at the $D_2$ receptors at concentrations as high as 3.2 mg/kg. These data also indicate that both compounds 38 and 52 are highly selective for the $D_3$ receptor over the $D_2$ receptor in vivo.

To further assess in vivo functional activity at the $D_3$ and $D_2$ receptors, compounds 38 and 52 were evaluated for their interactions with pramipexole in yawning and hypothermia assays in rats and compared them to known $D_2$ antagonist L-741,626 and $D_3$ antagonist SB-277011A. Similar to previous reports, the $D_3$ antagonist SB-277011A at 32 mg/kg inhibited the induction of yawning induced by both 0.1 mg/kg and 0.32 mg/kg of pramipexole.[39],[40] The $D_2$ antagonist L-741,626 reversed the inhibition of yawning observed at 0.32 mg/kg of pramipexole, but failed to alter the induction of yawning by 0.1 mg of pramipexole. These data are consistent with previous findings that pramipexole functions as a full agonist at the $D_3$ receptor at 0.1 mg/kg, but acts as an agonist at both the $D_3$ and $D_2$ receptors at 0.32 mg/kg.[36],[37]

Similar to the effects of $D_3$ antagonist SB-277011A achieved at 32 mg/kg, compounds 38 and 52 at 3.2 mg/kg effectively inhibited the induction of yawing by 0.1 mg/kg of pramipexole, and both compounds also reduced the amount of yawning produced by 0.32 mg/kg of pramipexole. Importantly, there were no significant differences between the amount of yawing produced by 3.2 mg/kg of compound 38 or compound 52, and the amount of yawning observed when 3.2 mg/kg compound 38 or compound 52 was administered as a 30-min pretreatment to a fully effective dose of pramipexole, consistent with the receptor theory on partial agonists.[7]

In addition, unlike the increases in yawning observed when L-741,626 was administered before an inhibitory dose of pramipexole, administration of compound 38 or compound 52 at a dose of 3.2 mg/kg failed to increase the amount of yawning induced by a high dose of pramipexole, illustrating that they are devoid of $D_2$ antagonist activity at 3.2 mg/kg. Taken together, these interaction data provide further evidence that compounds 38 and 52 are functioning as partial agonists at the $D_3$ receptor in vivo. Interestingly, compounds 38 and 52 also were capable of producing slight, but significant reductions in the hypothermic effects of pramipexole, suggesting that both compounds acted at the $D_2$ receptor when administered at a dose of 10.0 mg/kg (FIG. 2E). When taken together with the capacity of compounds 38 and 52 to induce slight decreases in body temperature on their own, and their inability to reverse the inhibitory effects of high doses of pramipexole on yawning, these findings suggest that compounds 38 and 52 are also functioning as partial agonists at the $D_2$ receptor in vivo at 10 mg/kg. Collectively, the in vivo profiles provided by the yawning and hypothermia assays clearly show that compounds 38 and 52 function as highly active partial agonists at the $D_3$ receptor and display a superb selectivity over the $D_2$ receptor.

In summary, a series of enantiomerically pure compounds of structural formula (I) and (II) have been synthesized, and their binding and selectivity to the $D_3$, $D_1$-like and $D_2$-like receptors has been evaluated. The present invention therefore identifies several potent and highly selective $D_3$ ligands with excellent aqueous solubility. In vivo functional evaluations show that compounds 38 and 52 function as $D_3$ partial agonists, are active at doses as low as 0.0032 mg/kg, and are devoid of any $D_2$ activity at 3.2 mg/kg, thus showing over 1000-fold selectivity at the $D_3$ receptor over the $D_2$ receptor.

The present invention therefore is directed to a class of potent and selective $D_3$ ligands that are highly potent and selective for the $D_3$ receptor over the other dopamine receptor subtypes and that have a unique of pharmacological and behaviorial profile. The present ligands have the therapeutic potential for the treatment of, for example, drug abuse, Parkinson's diseases, restless leg syndrome, and other conditions in which modulation of the $D_3$ receptor is desirable.

Experimental Protocols

In Vitro Dopamine Receptor Binding Assays

All the synthesized compounds were determined for the binding affinities at the $D_3$, $D_1$-like and $D_2$-like receptors in membranes prepared from the brains of adult, male Sprague-Dawley rats (Pel-Freez, Rogers, Ark.). All compounds were dissolved in 100% EtOH at a concentration of 5 mM.

[$^3$H]R(+)-7-OH-DPAT Binding Assays.

[$^3$H]R-(+)-7-OH-DPAT binding assays for the $D_3$ dopamine receptors were performed as previously described in detail.[44],[45] Rat ventral striatum (nucleus accumbens and olfactory tubercles) was prepared in assay buffer (50 mM Tris, 1 mM EDTA; pH 7.4 at 23° C.) to yield a final concentration of 10 mg original wet weight (o.w.w.)/ml. Membranes were incubated with [$^3$H]R-(+)-7-OH-DPAT (0.15 nM, SA=143 Ci/mmol; GE Healthcare) and various concentrations of competing compounds ($10^{-10}$ to $10^{-4}$ M). Nonspecific binding was defined by 1 µM spiperone. Assay tubes were incubated at 23° C. for 90 min. The reaction was terminated by rapid vacuum filtration. Data were analyzed using SigmaPlot 8.0.2. using the $K_D$ value for [$^3$H]7-OH-DPAT of 0.15 nM.[44] $K_i$ values are expressed at the mean±SEM of 3-6 independent determinations.

[$^3$H]Spiperone Binding Assays.

[$^3$H]spiperone binding assays for $D_2$-like receptors were performed as previously described in detail[45],[46] and as described for [$^3$H] 7-OH-DPAT except for the following. Assays were performed using membranes prepared from rat caudate-putamen, which expresses $D_2$ receptors in high density but very low levels of $D_3$ receptors, and the final membrane homogenate concentration was 1.5 mg o.w.w./ml. The assay buffer was 50 mM Tris-HCl, 5 mM KCl, 2 mM $MgCl_2$, and 2 mM $CaCl_2$, pH 7.4 at 23° C.; the concentration of [$^3$H]spiperone (24 Ci/mmol; GE Healthcare) was 0.2 nM; and the incubation time was 90 min at 23° C. Nonspecific binding was defined in the presence of 1 µM (+)-butaclamol. $K_i$ values were calculated using the experimentally-determined $K_D$ value for [$^3$H]spiperone of 0.4 nM.

[$^3$H]SCH 23390 Binding Assays.

[$^3$H] SCH 23390 binding assays for $D_1$-like dopamine receptors were performed as previously described in detail[45] and as described for [$^3$H]spiperone binding except the concentration of [$^3$H]SCH 23390 (73 Ci/mmol; GE Healthcare) was 0.3 nM. $K_i$ values were calculated using the $K_D$ value for [$^3$H]SCH 23390 of 0.3 nM.[45]

In Vivo Yawning and Hypothermia Assays in Rats

Animals and Drugs:

Male Sprague-Dawley rats (Harlan; Indianapolis, Ind.) weighing 250-300 g were housed three to a cage for yawning studies, and one to a cage for hypothermia studies, and maintained on a 12-h dark/light cycle with lights on at 7:00 AM in a temperature (21-23° C.) and humidity controlled environment with free access to standard Purina rodent chow and water. Pramipexole, compounds 38 and 52 were dissolved in sterile water, whereas SB-277011A was dissolved in 20%

β-cyclodextrin, and L-741,626 was dissolved in 5% ethanol and water. All drugs were administered subcutaneously (s.c.) in a volume of 1 ml/kg.

All studies were performed in accordance with the Guide for the Care and Use of Laboratory Animals, as adopted and promulgated by the National Institutes of Health, and all experimental procedures were approved by the University of Michigan Committee on the Use and Care of Animals.

Induction of Yawning Behavior:

Yawning behavior was defined as a prolonged (~1 sec.), wide opening of the mouth followed by a rapid closure. On the day of testing, rats were transferred from their home cage to a test chamber (48 cm×23 cm×20 cm clear rodent cage with standard cob bedding), and allowed to habituate to the chamber for a period of 30 min prior to a sterile water injection which was administered 30 min prior to the injection of the compound of interest. Yawns were scored for a period of 60 min thereafter. Each compound was assessed in groups of 6 rats, with each rat receiving a single dose of one compound. Food and water were unavailable during test sessions, and all experiments were conducted between the hours of 12:00 PM and 6:00 PM with at least 72 hrs between test sessions to allow for drug washout.

Measurement of Core Body Temperature:

Rats were anesthetized with ketamine/xylazine (100/10 mg/kg; i.p.) and their abdominal area was shaved and cleaned with alternating betadine and alcohol swabs prior to surgical implantation of radio-telemetric probes (E-4000 E-Mitter, Mini-Mitter, Bend, Oreg., USA). A small rostral-caudal incision was made in the abdominal wall to allow for insertion of the probe, and the abdominal wall was closed using absorbable, 5-0 chromic gut suture, and the skin was closed using 5-0 Ethilon® suture. A 7-day recover period was provided prior to experimentation.

On the day of testing, rats were weighed and returned to their home cages, which were placed onto a receiving pad (ER-4000 Receiver, Mini-mitter, Bend, Oreg.) to allow for the collection of core body temperature. Temperature measurements were taken every min with at least 30 min of baseline temperature data recorded prior to the administration of antagonist or vehicle. Agonist or vehicle injections were administered 30 min thereafter, and core body temperature was recorded for a period of at least the next 60 min. Rats were removed from the receivers for a period of 5 min to allow for injections to be administered, but were otherwise uninterrupted. Each rat was tested at each dose condition, with at least a 72 hrs between test sessions. All experiments were carried out between the hours of 12:00 PM and 6:00 PM.

Effects of Compounds 38 and 52 on Pramipexole-Induced Yawning and Hypothermia:

Measures of yawning behavior and core body temperature were performed as described above with the exception that compound 38, compound 52, SB-277011A, or L-741,626 were administered 30 min prior to doses of 0.1 or 0.32 mg/kg pramipexole in yawning studies, and 1.0 mg/kg pramipexole for hypothermia studies. Compound 38 or compound 52 was administered at doses of 3.2 mg/kg for yawning studies, and 10.0 mg/kg for hypothermia studies, whereas SB-277011A and L-741,626 were administered at 32.0 mg/kg and 1.0 mg/kg, respectively, for both yawning and hypothermia studies. Briefly, following a 30 min habituation period, rats were administered either vehicle, or one dose of compound 16, 30 min prior to a dose of pramipexole. Observation of yawning behavior began immediately after each injection, and the total number of yawns was recorded for 60 min thereafter. Core body temperature was continuously measured for at least 60 min after pramipexole administration.

Data Analysis:

Dose-response curves for the induction of yawning and hypothermia were determined with 6 rats per group, and results expressed as the mean number of yawns, or change in body temperature 60 min post agonist injection compared to the body temperature 1 min prior to the agonist injection±standard error of the mean (SEM). The effects experimental compounds on pramipexole-induced yawning and hypothermia, are expressed as the mean number of yawns or change in body temperature observed during the 60-min period immediately following pramipexole administration. One-way, repeated-measures ANOVA with post-hoc Newman-Keuls tests were used to determine if compounds induced significantly more yawning or hypothermia as compared to vehicle, as well as to determine if pretreatments significantly altered pramiepxole-induced yawning or hypothermia (GraphPad Prism; GraphPad Software Inc., San Diego, Calif.).

REFERENCES (1) J. N. Joyce. *Pharmacol. Ther.* 2001, 90, 231-259.
(2) S. Prasad et al. *J. Biosci.* 2002, 27 (1, Suppl. 1), 35-52.
(3) M. A. Crocg et al. *Trends Mol. Med.* 2003, 9, 360-365.
(4) N. D. Volkow et al. *Behav. Pharmacol.* 2002, 13, 355-366.
(5) R. R. Luedtke et al. *Curr. Pharm. Des.* 2003, 9, 643-671.
(6) M. Pilla et al. *Nature* 1999, 400, 371-375.
(7) A. Newman et al. *J. Med. Chem.* 2005, 48, 3663-3679.
(8) C. A. Heidbreder et al. *Ann N Y Acad. Sci.* 2010, 1187, 4-34.
(9) C. Reavill et al. *J. Pharmacol. Exp. Ther.* 2000, 294, 1154-1165.
(10) J. Yuan et al. *Bioorg. Med. Chem. Lett.* 1998, 8, 2715-2718.
(11) M. J. Robarge et al. *J. Med. Chem.* 2001, 44, 3175-3186.
(12) L. Bettinetti et al. *J. Med. Chem.* 2002, 45, 4594-4597.
(13) A. Hackling et al. *J. Med. Chem.* 2003, 46, 3883-3899.
(14) M. Leopoldo et al. *J. Med. Chem.* 2002, 45, 5727-5735.
(15) G. Campiani et al. *J. Med. Chem.* 2003, 46, 3822-3839.
(16) G. J. Macdonald et al. *J Med Chem.* 2003, 46, 4952-4964.
(17) G. Campiani et al. *J. Med. Chem.* 2004, 47, 143-157.
(18) P. Grundt et al. *J. Med. Chem.* 2005, 48, 839-848.
(19) J. Varady et al. *J. Med. Chem.* 2003, 46, 4377-4392.
(20) S. R. Haadsma-Svensson et al. *J. Med. Chem.* 2001, 44, 4716-4732.
(21) M. Ji et al. *Bioorg. Med. Chem. Lett.* 2005, 15, 1701-1705.
(22) K. Ding et al. *J. Med. Chem.* 2005, 48, 3171-3181.
(23) J. Chen et al. *Bioorg. Med. Chem. Lett.* 2006, 16, 443-446.
(24) K. Ehrlich et al. *J. Med. Chem.* 2009, 52, 4923-4935.
(25) J. Chen et al. *J. Med. Chem.* 2008, 51, 5905-5908.
(26) F. Micheli et al. *J. Med. Chem.* 2010, 53, 7129-7139.
(27) S. Biswas et al. *J. Med. Chem.* 2008, 51, 3005-3019.
(28) D. A. Brown et al. *J. Med. Chem.* 2008, 51, 7806-7819.
(29) B. Ghosh et al. *J. Med. Chem.* 2010, 53, 2114-2125.
(30) P. Grundt et al. *J. Med. Chem.,* 2007, 50, 4135-4146.
(31) A. H. Newman et al. *J. Med. Chem.,* 2009, 52, 2559-2570.
(32) F. Micheli et al. *J Med. Chem.* 2010, 53, 374-391.
(33) F. Micheli et al. *J Med. Chem.* 2010, 53, 7129-39.

(34) M. D. Wood et al. *Eur. J. Pharmacol.* 2000, 407, 47-51.
(35) K. Wicke et al. *Eur. J. Pharmacol.* 2001, 424, 85-90.
(36) G. T. Collins et al. *J. Pharmacol. Exp. Ther.* 2005, 314, 310-319.
(37) G. T. Collins et al. *Psychopharmacology* (Berl) 2007, 193, 159-170.
(38) M. G. Baladi et al. *J. Pharmacol. Exp. Ther.* 2009, 332, 308-315.
(39) G. T. Collins et al. *J. Pharmacol. Exp. Ther.* 2008, 325, 691-697.
(40) G. T. Collins et al. *J. Pharmacol. Exp. Ther.* 2009, 329, 210-217.
(41) D. Boulay et al. *Neuropharmacology* 1999, 38, 1389-1396.
(42) F. Chaperon et al. *Neuropharmacology* 2003, 44, 1047-1053.
(43) M. Fujikawa et al. *Pharmacol. Biochem. Behav.* 1996, 53, 903-909.
(44) G. N. Bancroft et al. *Neuropsychopharmacology*, 1998, 18, 305-316.
(45) B. Levant. *Current Protocols in Pharmacology* (J Ferkany and S J Enna, Eds). 1998, John Wiley & Sons, New York, pp. 1.6.1-1.6.16.
(46) B. Levant et al. *J. Pharmacol. Exp. Ther.* 1992, 262, 929-935.

What is claimed:

1. A compound having a structural formula

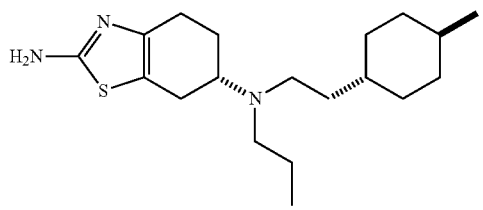

wherein $R^1$ is $C_{1-6}$ alkyl or $C_{3-6}$ cycloalkyl; and wherein $R^1$ is methyl, ethyl, isopropyl, cyclopropyl,

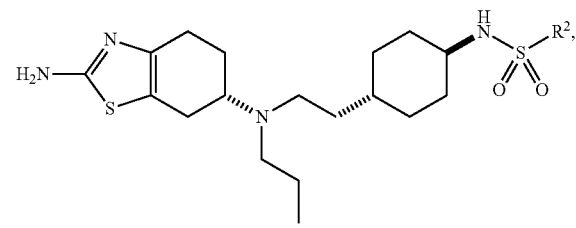

wherein $R^2$ is

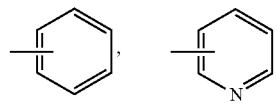

substituted with one, two halogen(s), $OC_{1-3}$alkyl.

2. The compound of claim 1 wherein

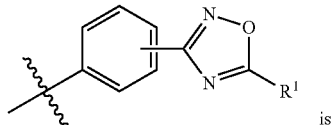

is

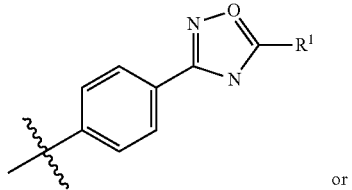

or

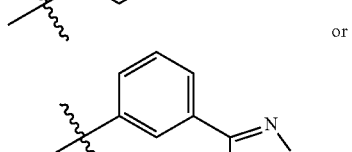

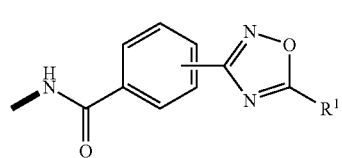

3. A compound having a structural formula

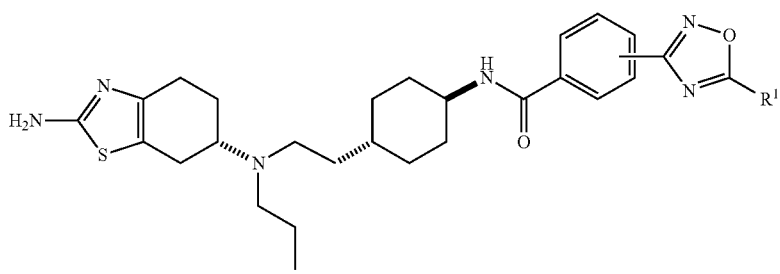

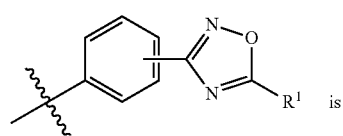 is 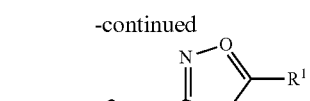 or

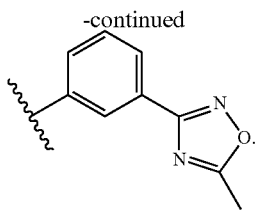

-continued

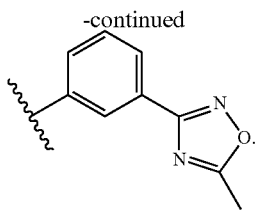

4. A compound selected from the group consisting of

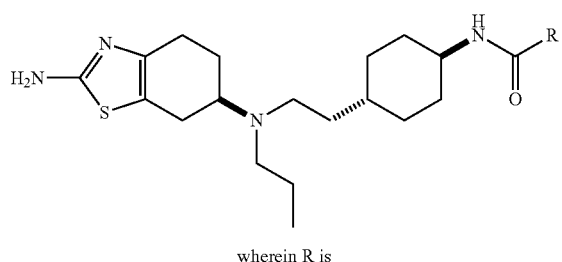

wherein R is

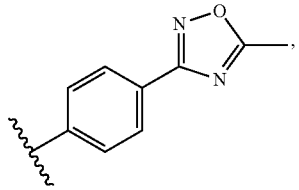,

,

,

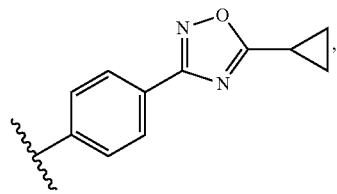,

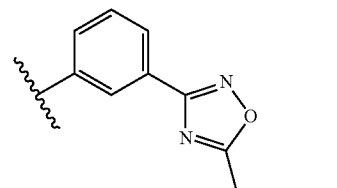, or

5. A method of treating a disease or condition wherein modulation of dopamine $D_3$ receptors provides a benefit comprising administering a compound of claim 1 to an individual having a disease selected from the group consisting of drug abuse, Parkinson's disease, restless leg syndrome, schizophrenia, and depression.

6. The method of claim 5 further comprising administering a therapeutically effective amount of a second therapeutic agent useful in the treatment of the disease or condition selected from the group consisting of drug abuse, Parkinson's disease, restless leg syndrome, schizophrenia, and depression.

7. The method of claim 5 wherein the compound of claim 1 and the second therapeutic agent are administered simultaneously.

8. The method of claim 6 wherein the compound of claim 1 and the second therapeutic agent are administered from a single composition.

9. The method of claim 6 wherein the compound of claim 1 and the second therapeutic agent are administered from separate compositions.

10. The method of claim 9 wherein the compound of claim 1 is administered prior to the second therapeutic agent.

11. The method of claim 9 wherein the compound of claim 1 is administered after the second therapeutic agent.

12. The method of claim 6 wherein the second therapeutic agent is selected from the group consisting of an antipsychotic agent, an antidepressant agent, a monoamine oxidase inhibitor, a 5-HT reuptake inhibitor, a serotonin-1 B antagonist, a serotonin-2A antagonist, a histamine-3 antagonist or agonist, and an antiparkinsonian agent.

13. The method of claim 12 wherein the second therapeutic agent is selected from the group consisting of clozapine, olanzapine, quetiapine, risperidone, ziprasidone, haloperidol, aripiprazole, a tricyclic antidepressant, amitriptyline, dothiepin, doxepin, trimipramine, butriptyline, clomipramine, desipramine, imipramine, iprindole, lofepramine, nortriptyline, protriptyline, isocarboxazid, phenelzine, tranylcyclopramine, fluvoxamine, sertraline, fluoxetine, paroxetine, elzasonan, eplivanserin, MDL-100907, cipralisant, ABT239, TISQ, GSK-189254A, a dopaminergic antiparkinsonian agent, and levodopa, alone or in combination with a peripheral decarboxylase inhibitor, benserazide, or carbidopa, or with a dopamine agonist, bromocriptine, lysuride, or pergolide, and mixtures thereof.

14. A kit comprising:
   (a) a packaged composition comprising a compound of claim 1;
   (b) optionally, a packaged composition comprising a second therapeutic agent useful in a treatment of a disease or condition wherein modulation of $D_3$ receptors provide a benefit;
   (c) an insert providing instructions for a simultaneous or sequential administration (a), or (a) and (b), to treat a disease or condition wherein modulation of $D_3$ receptors provide a benefit in a human;
   (d) a container for (a), (b), and (c),
   wherein the disease or condition is selected from the group consisting of drug abuse, Parkinson's disease, restless leg syndrome, schizophrenia, and depression.

15. A composition comprising (a) compound of claim 1, (b) a second therapeutic agent useful in the treatment of a disease or condition wherein modulation of $D_3$ receptors provide a benefit, and (c) an optional excipient and/or pharmaceutically acceptable carrier,
   wherein the disease or condition is selected from the group consisting of drug abuse, Parkinson's disease, restless leg syndrome, schizophrenia, and depression.

* * * * *